US008852939B2

(12) United States Patent
Hall et al.

(10) Patent No.: US 8,852,939 B2
(45) Date of Patent: Oct. 7, 2014

(54) USE OF VGLL3 ACTIVITY MODULATOR FOR THE MODULATION OF ADIPOGENESIS

(75) Inventors: Diana Hall, Lausanne (CH); Maria Jimenez, Chavannes-pres-renens (CH); Carine Poussin, Evian-les-Bains (FR); Bernard Thorens, Epalinges (CH)

(73) Assignee: Sanofi, Paris (FR)

( * ) Notice: Subject to any disclaimer, the term of this patent is extended or adjusted under 35 U.S.C. 154(b) by 113 days.

(21) Appl. No.: 13/201,011

(22) PCT Filed: Feb. 16, 2010

(86) PCT No.: PCT/IB2010/050692
§ 371 (c)(1),
(2), (4) Date: Oct. 4, 2011

(87) PCT Pub. No.: WO2010/095096
PCT Pub. Date: Aug. 26, 2010

(65) Prior Publication Data
US 2012/0101150 A1  Apr. 26, 2012

(30) Foreign Application Priority Data

Feb. 18, 2009 (EP) ..................................... 09290115

(51) Int. Cl.
*A61K 48/00* (2006.01)
*A01N 63/00* (2006.01)
*C12N 5/02* (2006.01)
*C12P 21/04* (2006.01)
*C07K 14/46* (2006.01)
*G01N 33/68* (2006.01)
*G01N 33/53* (2006.01)

(52) U.S. Cl.
CPC ............ *G01N 33/6872* (2013.01); *C07K 14/46* (2013.01); *G01N 2800/044* (2013.01); *G01N 33/53* (2013.01); *C12N 2800/107* (2013.01); *A61K 48/005* (2013.01)
USPC .......... 435/377; 424/93.1; 435/70.1; 514/44 R

(58) Field of Classification Search
CPC ........... A61K 48/005; C12N 2800/107; G01N 2800/107; G01N 2800/044; G01N 33/53
USPC ................. 424/93.1; 435/70.1, 377; 514/44 R
See application file for complete search history.

(56) References Cited

U.S. PATENT DOCUMENTS

| 5,399,346 | A | 3/1995 | Anderson |
| 5,580,859 | A | 12/1996 | Felgner et al. |
| 5,589,466 | A | 12/1996 | Felgner et al. |
| 7,745,391 | B2 | 6/2010 | Mintz et al. |
| 2006/0134663 | A1 | 6/2006 | Harkin et al. |
| 2007/0083334 | A1 | 4/2007 | Mintz et al. |
| 2007/0099251 | A1 | 5/2007 | Zhang et al. |
| 2009/0012024 | A1 | 1/2009 | Collins et al. |
| 2009/0221437 | A1 | 9/2009 | Harkin et al. |
| 2011/0287974 | A1 | 11/2011 | Benvenisty et al. |
| 2012/0087862 | A1 | 4/2012 | Hood et al. |

FOREIGN PATENT DOCUMENTS

| WO | WO 97/10343 | 3/1997 |
| WO | WO 2008/085601 A2 | 7/2008 |

OTHER PUBLICATIONS

Strausberg et al., Generation and initial analysis of more than 15,000 full-length human and mouse cDNA sequences Proc Natl Acad Sci U S A. Dec. 24, 2002; 99(26): 16899-16903.*
Soubrier et al., pCOR: a new design of plasmid vectors for nonviral gene therapy, Gene Therapy, vol. 6, 1999, pp. 1482-1488.
Banerjee et al., The Kruppel-like Factor KLF2 Inhibits Peroxisome Proliferator activated Receptor-γ Expression and Adipogenesis, J. of Biol. Chem., vol. 278, No. 4, Jan. 24, 2003, pp. 2581-2584.
Chen et al., Krox20 stimulates adipogenesis via C/EBP Beta-dependent and -Independent mechanisms, Cell Metabolism, vol. 1, Feb. 2005, pp. 93-106.
Chen et al., Transcription Cofactor Vgl-2 is Required for Skeletal Muscle Differentiation, Genesis, vol. 39, 2004, pp. 273-279.
Collins et al., Genetic vulnerability to diet-induced obesity in the C57BL/6J mouse: physiological and molecular characteristics. Physiology & Behavior, vol. 81, 2004, pp. 243-248.
De Fourmestraux et al., Transcript Profiling Suggests That Differential Metabolic Adaptation of Mice to a High Fat Diet Is Associated with Changes in Liver to Muscle Lipid Fluxes, J. of Biol. Chem., vol. 279, No. 49, Dec. 3, 2004, pp. 50743-50753.
Gray et al., The Kruppel-like Factor KLF15 Regulates the Insulin-sensitive Glucose Transporter GLUT4, J. of Biol. Chem, vol. 277, No. 37, Sep. 13, 2002, pp. 34322-34328.
Jimenez et al., Critical Role for Ebf1 and Ebf2 in the Adipogenic Transcriptional Cascade, Molecular and Cellular Biology, vol. 27, No. 2, Jan. 2007, pp. 743-757.
Kang et al., Wnt Signaling Stimulates Osteoblastogenesis of Mesenchymal Precursors by Suppressing CCAAT/Enhancer-binding Protein and Peroxisome Proliferator-activated Receptor γ, J. of Biol. Chem, vol. 282, No. 19, May 11, 2007, pp. 14515-14524.
Maeda et al., Mammalian Vestigial-like 2, a Cofactor of TEF-1 and MEF2 Transcription Factors That Promotes Skeletal Muscle Differentiation, J of Biol. Chem., vol. 277, No. 50, Dec. 13, 2002, pp. 48889-48896.
Mielcarek et al., VITO-2, a new SID domain protein, is expressed in the myogenic lineage during early mouse embryonic development, Gene Expression Patterns, vol. 9, 2009, pp. 129-137.
Paumard-Rigal et al., Specific interactions between vestigial and scalloped are required to promote wing tissue proliferation in *Drosophila melanogaster*, Dev. Genes Evol., vol. 208, 1998, pp. 440-446.

(Continued)

*Primary Examiner* — Maria Leavitt
(74) *Attorney, Agent, or Firm* — Lathrop & Gage LLP; James H. Velema, Esq.

(57) ABSTRACT

The present invention concerns Vgll3 a new target involved in adipogenesis modulation. Further, the present invention relates to methods to increase Vgll3 activity in adipocytes and preadipocytes. In addition, pharmaceutical composition comprising Vgll3 activity enhancing molecules in order to enhance the Vgll3 activity in a target tissue are also provided. These methods, compositions and molecules can be useful to modulate adipogenesis and thus treat obesity and related disorders.

8 Claims, 4 Drawing Sheets

(56) References Cited

OTHER PUBLICATIONS

Poussin et al., Different Transcriptional Control of Metabolism and Extracellular Matrix in Visceral and Subcutaneous Fat of Obese and Rimonabant Treated Mice, PLoS ONE, vol. 3, No. 10, Oct. 2008, e3385, p. 1-14.

Rosen et al., C/EBPalpha induces adipogenesis through PPARg: a unified pathway, Genes & Development, vol. 16, 2002, pp. 22-26.
International Search Report for WO2010/095096 dated Aug. 26, 2010.
Written Opinion from International Application No. PCT/IB2010/050692 dated Apr. 4, 2010.

* cited by examiner

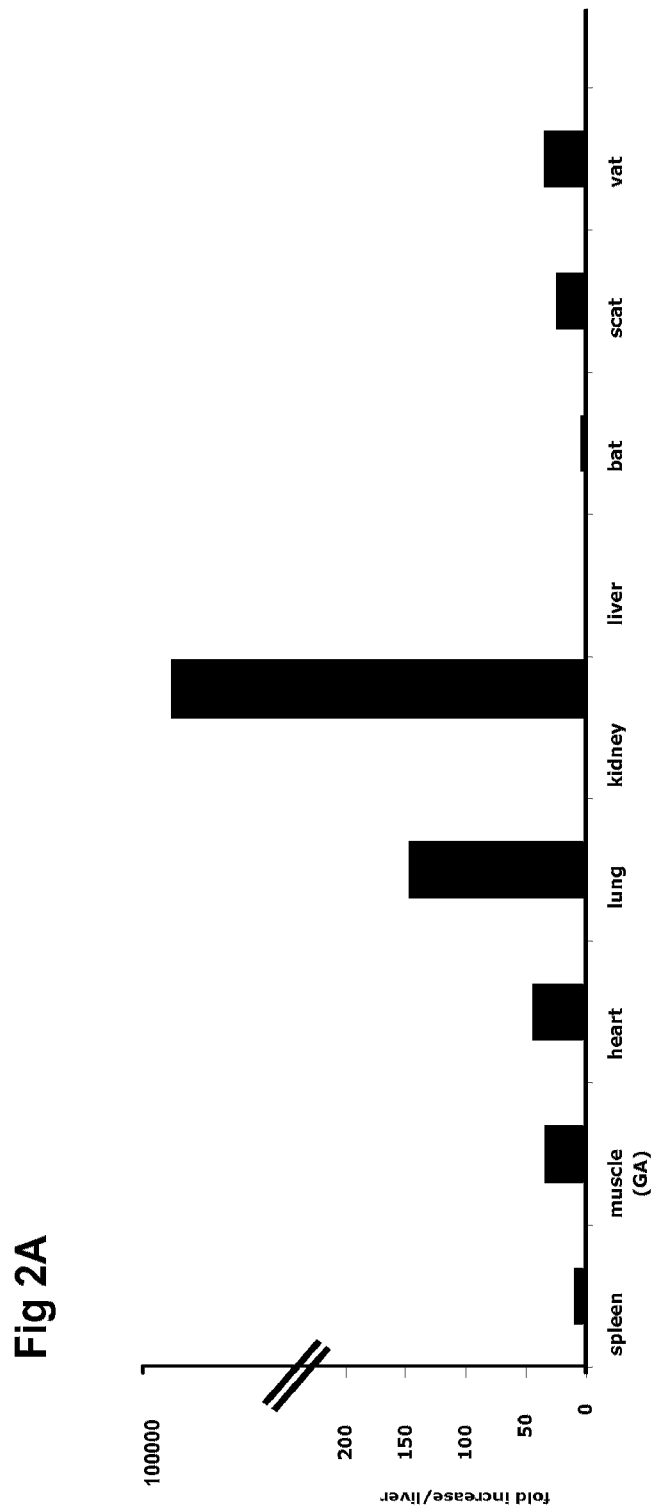

USE OF VGLL3 ACTIVITY MODULATOR FOR THE MODULATION OF ADIPOGENESIS

The present invention concerns Vgll3 a new target involved in adipogenesis modulation.

Further, the present invention relates to methods to increase Vgll3 activity in adipocytes and preadipocytes. In addition, pharmaceutical compositions comprising a molecule for enhancing Vgll3 activity in a target tissue are also provided. These methods, compositions and molecules can be useful to modulate adipogenesis and thus treat obesity and related disorders.

Obesity is a major risk factor for a number of disorders including hypertension, coronary artery disease, dyslipidemia, insulin resistance and type 2 diabetes. Because of the importance of the obesity epidemic, a great deal of investigation has centered on the biology of the adipocyte, including the developmental pathway by which new adipocytes are created. Adipogenesis is the process by which undifferentiated mesenchymal precursor cells become mature adipocytes. Throughout the last decade considerable progress has been made in elucidating the molecular mechanisms of adipocyte differentiation, which involve sequential activation of transcription factors from several families such as CCAAT/ enhancer binding proteins (C/EBPα, α, and γ) and the nuclear hormone receptor peroxisome proliferator-activated receptor γ (PPARγ) (Rosen, E. D. et al., 2002). PPARγ is described as a "master regulator" of adipogenesis since it has been shown to be both sufficient and necessary for adipogenesis both in vitro and in vivo. Recently, new transcription factors have been described to participate in adipogenesis such as KLF family (KLF2, 5 and KLF15) (Banerjee, S. S. et al., 2003; Gray, S. M. et al., 2002), Ebf family (Jimenez, M. A. et al., 2007) and Krox 20 (Chen, Z. et al., 2005), suggesting that the transcriptional cascade occurring during adipogenesis is much more complex than previously thought. Furthermore, signaling molecules and/or receptors such as the Wnt family of secreted proteins (Kang S. et al., 2007), sonic hedgehog protein, Notch receptor have also been described to be involved in molecular events leading to adipocyte formation. It is interesting to note that extracellular and intracellular events are somehow coupled to regulate adipogenesis. All these signaling pathways converge on a tightly regulated transcriptional cascade, which needs to be more completely understood to potentially control adipocyte development and prevent obesity.

Storage of fat in adipose tissue is limited and exceeding this capacity leads to accumulation of lipids in others tissues, in particular in muscle, liver, and the endocrine pancreas, and to the secretion by adipocytes of various adipokines. The adipose tissue consists of several deposits located at different anatomical sites which may originate from distinct precursors and which have different physiological functions and pathophysiological roles. The visceral, as opposed to the subcutaneous adipose depots, may contribute more to the defects associated with the metabolic syndrome.

Cannabinoid 1 receptors have been identified in all organs playing a key role in glucose metabolism and type 2 diabetes, i.e. adipose tissue, the gastrointestinal tract, the liver, the skeletal muscle and the pancreas. Rimonabant, the first selective cannabinoid receptor 1 (CB1R) antagonist in clinical use, has been shown to reduce food intake and body weight thus improving glucose metabolism regulation.

However, there is still a need for novel therapeutic targets for the treatment of obesity.

Vestigial-like 3 factor (Vgll3) belongs to the vestigial family, which contains 3 members. It was first described in Drosophila melanogaster as a co-factor of transcription that might be involved in wing development (Paumard-Rigal, S. et al., 1998). Vgll3 is located inside the nucleus and might interact with the adipogenic transcriptional cascade. Recently the second member, Vgll2, has been linked to muscle development in mammals (Chen, H. H., T., et al., 2004). This family of proteins is expressed in precursor cells that presumably commit to either adipocyte or muscle cells.

The inventors have now found that Vgll3 plays a critical role in adipocyte differentiation. Vgll3 is therefore considered as a new relevant target for modulation of adipogenesis, and thus for the treatment of obesity and related disorders. Overexpression of Vgll3 can also be used for reduction of adipogenesis for reduction of visceral and/or subcutaneous fat accumulation.

DETAILED DESCRIPTION OF THE INVENTION

The present invention is dawn to methods for regulation of adipogenesis and metabolic function in adipocytes and preadipocytes.

The present invention consists in Vgll3 activity enhancing molecules able to increase Vgll3 activity in preadipocytes or adipocytes. Such molecules are useful to obtain a reduction of visceral and/or subcutaneous fat. They thus can be used for the preparation of a medicament to reduce adipogenesis, in particular for treatment of obesity and related disorders.

As used herein, the term "Vgll3 activity enhancing molecules" encompasses compounds able to increase Vgll3 activity and vectors expressing a Vgll3 recombinant protein. These two kinds of molecules are described in details below.

As used herein, the term "related disorders" in "obesity and related disorders" encompasses hypertension, coronary artery disease, dyslipidemia, insulin resistance and type 2 diabetes.

Through a transcriptomic approach, the inventors identified genes whose expression was correlated with body weight gain in cohorts of C57Bl/6 mice fed a high fat diet. Then, they conducted a second analysis in order to evaluate the changes in gene expression induced by Rimonabant treatment of the high fat diet fed mice. Genes which have never been described before in adipocyte biology, but which might be involved in important biological processes such as signaling, modification of extracellular matrix proteins, and gene transcription were retained. These genes could be important for adipogenesis especially since they might be involved in the mechanism by which Rimonabant reduces fat mass in mice. In this context, Vgll3 was identified as involved in adipocytes metabolism, especially in new signaling pathway. More generally, this gene appears to play a role in adipogenesis and control of adipose tissue development in obesity.

Enhancing Vgll3 activity in adipocytes and preadipocytes can be useful in therapeutics to modulate adipogenesis, especially to reduce adipogenesis, in particular in the treatment and prevention of obesity related disorders, which are type 2 diabetes, dyslipidemia, elevated blood pressure, insulin resistance, cardiovascular disorders and more generally metabolic syndromes.

Enhancing Vgll3 activity in adipocytes and preadipocytes can also be useful for cosmetic applications in order to reduce disgraceful fat accumulation.

In one embodiment, Vgll3 activity can be increased in adipocytes and preadipocytes using small molecules that enhance the transcription of Vgll3. Such compounds able to increase Vgll3 activity can be identified using methods well known by the person skilled of the art. One method can be a reporting system consisting in the promoter of Vgll3 linked in frame to a reporter gene and expressed in a suitable cell line; the reporter gene product's activity can be quantitatively measured. Thus, a compound that enhances the expression of the reporter gene can be considered as a potential candidate.

The reporter genes that can be used in such reporting systems are numerous and well known in the art. For example, such reporter genes can be genes allowing expression of Green Fluorescent Protein (GFP), luciferase, Beta-galactosidase, . . . .

Therefore, on aspect of the present invention is to provide a method for screening for enhancers of the activity of Vgll3 which comprises the steps of:
a) transfecting a cell line with a reporter construction comprising a Vgll3 promoter linked to a reporter gene
b) cultivating said cell line in condition to allow expression of the reporter gene
c) adding candidate compounds into the cell culture
d) identifying enhancer compounds as being those compounds which have the ability to increase the reporter gene expression.

The predicted promoter of human Vgll3 which can be used in the described above screening test for modulators of Plac8 transcription corresponds to SEQ ID NO.17.

In another embodiment, enhancing of the Vgll3 activity in a patient in need thereof can be obtained by administration of a recombinant vector bearing a sequence for Vgll3 expression.

With this aim, the present invention provides vectors comprising polynucleotides for expression of a Vgll3 recombinant protein. These vectors can be naked DNA, or viral vector such as adenoviral vector, AAV vector or retroviral vector as lentiviral vector. These vectors can be administered by different suitable routes including intravenous route or local injection including intramuscular route, direct injection into subcutaneous tissue or other targeted tissue chosen according to usual practice.

In one embodiment, the expression vector is a plasmid. Such a plasmid may be a conditionally replicating plasmid that is incapable of replicating in the patients for safety reasons. These plasmids may be based on the plasmid pCOR as described in the patent publication WO 97/10343. The vector may comprise a promoter capable of directing expression of the Vgll3 polypeptide in the tissue to which it is administered, such as the cytomegalovirus immediate early promoter. The vector may further comprise a polyadenylation signal from SV40. The vector may be administered in a variety of ways, including by intramuscular injection. The vector may be administered by multiple injections directly in the ischemic muscles to be treated.

Thus, a Vgll3 recombinant protein may be provided by delivering such a plasmid vector to a cell in vivo, in vitro or ex vivo, and allowing transcription from the vector to occur. Preferably, a polynucleotide of the invention is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

Promoters and other expression regulation signals may be selected to be compatible with the host cell for which expression is designed. In particular, where the method of the invention requires direct delivery into a muscle, the promoters and other expression regulatory systems should be capable of functioning in muscle tissues. For example, mammalian promoters, such as β-actin promoters, may be used.

Examples of promoters useful to practice the present invention include but are not limited to viral promoters such as promoters from Simian Virus 40 (SV40) (e.g. the SV40 large T antigen promoter or SV40 early promoter), Mouse Mammary Tumor Virus (MMTV) (e.g. MMTV LTR promoter), Human Immunodeficiency Virus (HIV) (e.g. the HIV Long Terminal Repeat (LTR) promoter), Moloney virus (e.g. Moloney murine leukaemia virus LTR promoter), ALV, Cytomegalovirus (CMV) (such as the CMV immediate early promoter), Epstein Barr Virus (EBV), Rous Sarcoma Virus (RSV) (e.g. the RSV LTR promoter), adenovirus, (e.g. the adenovirus major late promoter Ad MLP), HSV (such as the HSV IE promoters), or HPV promoters (e.g. the HPV upstream regulatory region URR). Suitable promoters may also be derived from human genes such as human alpha or beta actin, human Myosin, human hemoglobin, human muscle creatine and human metallothionein or any suitable tissue-specific promoters. All these promoters are readily available in the art.

Examples of polyadenylation signals useful to practice the present invention include but are not limited to SV40 polyadenylation signals, bovine or human growth hormone polyadenylation signals, and LTR polyadenylation signals. In particular, the SV40 polyadenylation signal which is in pCEP4 plasmid (Invitrogen, San Diego Calif.), referred to as the SV40 polyadenylation signal may be used.

The vector may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

In one embodiment the Vgll3 encoding plasmid contains a conditional origin of replication in bacteria such as the plasmid pCOR as described in the International application WO 97/10343 and Soubrier et al. (*Gene Ther.* 1999; 6:1482-1488). Plasmids based on the pCOR backbone are also described in WO 2004/033664. The pCOR backbone is small (1 Kbp) as compared with conventional backbone (2 to 2.5 Kbp), thus reducing by half the amount of unwanted bacterial DNA injected into the patient.

In one embodiment, therefore, the pCOR plasmid may harbor an expression cassette encoding an Vgll3 recombinant protein as described above.

The vector may be a recombinant viral vector. Suitable recombinant viral vectors include but are not limited to adenovirus vectors, adeno-associated viral (AAV) vectors, herpesvirus vectors, a retroviral vector, lentiviral vectors, baculoviral vectors, pox viral vectors or parvovirus vectors.

The vector may be a targeted vector, that is a vector whose ability to infect or transfect or transduce a cell or to be expressed in a host and/or target cell is restricted to certain cell types within the host subject, usually cells having a common or similar phenotype.

The vectors and expression cassettes of the present invention may be administered directly as "a naked nucleic acid construct". As used herein, the term "naked DNA" refers to a vector such as a plasmid comprising a polynucleotide of the present invention together with a short promoter region to control its production. It is called "naked" DNA because the vectors are not carried in any delivery vehicle, for example they are free of viral components, particularly any viral particles which may carry genetic information. They are similarly free from, or naked with respect to, any material which promotes transfection, such as liposomal formulations, charged lipids such as Lipofectin™, or precipitating agents such as $CaPO_4$. When such a vector enters a host cell, such as a eukaryotic cell, the proteins it encodes are transcribed and translated within the cell.

A vector such as a plasmid may be delivered to the animal with a pharmaceutically acceptable liquid carrier. In preferred applications, the liquid carrier is aqueous or partly aqueous, comprising sterile, pyrogen-free water. The pH of the preparation is suitably adjusted and buffered. Suitable compositions for administration are described further below.

Alternatively, liposomal preparations can be used to deliver the vectors of the invention. Useful liposomal preparations include cationic (positively charged), anionic (negatively charged) and neutral preparations, with cationic liposomes particularly preferred. Cationic liposomes may mediate intracellular delivery of plasmid DNA and mRNA.

In the case of viral vectors, administration of the polynucleotide is mediated by viral infection of a target cell.

Systemic administration of vector expressing Vgll3 allows to transduce tissues which are not accessible from outside. For systemic delivery, Vgll3 protein can be formulated with cholesterol conjugate, liposomes or polymer-based nanoparticules. Liposomes are traditionally used in order to provide increased pharmacokinetics properties and/or decreased toxicity profiles. They allow significant and repeated success in vivo delivery.

Methods for gene delivery are known in the art. See, e.g., U.S. Pat. Nos. 5,399,346, 5,580,859 and 5,589,466. The vector can be introduced directly into the recipient subject, such as by standard intramuscular or intradermal injection; transdermal particle delivery; intravenous delivery, inhalation; topically, or by oral, intranasal or mucosal modes of administration. The vector can also be introduced in vitro or ex vivo into cells which have been harvested from a subject.

According to the present invention, the vector expressing a Vgll3 recombinant protein can bear the sequence SEQ ID NO.15 or its derivatives due to degeneration of genetic code or any derivatives thereof having at least 60, 70, 80, 90, 95, 98 or 99% of sequence identity with this sequence.

In a preferred embodiment, the vector expresses a Vgll3 recombinant protein having a sequence corresponding to SEQ ID NO.2 or SEQ IN NO.4 or derivatives or fragments or homologs of these sequences presenting at least 60, 70, 80, 90, 95, 98 or 99% of sequence identity with these sequences.

In another embodiment, these homologs, derivatives and fragments retain the same activity as Vgll3, or at least 50, 80 or 90% of this activity.

The invention also consists in a method for modulation of adipogenesis comprising the administration to a patient in need thereof of a Vgll3 activity enhancing molecule to modulate adipogenesis. Such method can be used to treat obesity or related diseases. Such method can also be used in order to decrease fat accumulation in a cosmetic purpose.

Another object of the invention is a composition which comprises a Vgll3 activity enhancing molecule according to the present invention. These compositions comprise an effective dose of at least one such molecule according to the invention, and at least one pharmaceutically acceptable excipient. This composition is useful for the preparation of a medicament to inhibit adipogenesis. In a preferred embodiment, it can be used to treat obesity and related diseases.

The composition can also be useful for reduction of visceral and/or subcutaneous fat accumulation.

Any suitable pharmaceutically acceptable carrier can be used within the context of the present invention, and such carriers are well known in the art. The choice of carrier will be determined, in part, by the particular site to which the composition is to be administered and the particular method used to administer the composition. Formulations suitable for injection include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid carrier, for example, water, immediately prior to use. Extemporaneous injection solutions and suspensions can be prepared from sterile powders, granules, and tablets of the kind previously described. Preferably, the pharmaceutically acceptable carrier is a buffered saline solution. Most preferably, the pharmaceutical composition is isotonic, for example comprises a solution of sodium chloride (0.9%).

Those skilled in the art can adjust the dosage and concentration to suit the particular route of delivery. In one embodiment, a single dose is administered on a single occasion. In an alternative embodiment, a number of doses are administered to a subject on the same occasion but, for example, at different sites. In a further embodiment, multiple doses are administered on multiple occasions. Such multiple doses may be administered in batches, i.e. with multiple administrations at different sites on the same occasion, or may be administered individually, with one administration on each of multiple occasions (optionally at multiple sites). Any combination of such administration regimes may be used.

The invention is now described by reference to the following examples, which are illustrative only, and are not intended to limit the present invention.

EXAMPLES

Figure 1A:
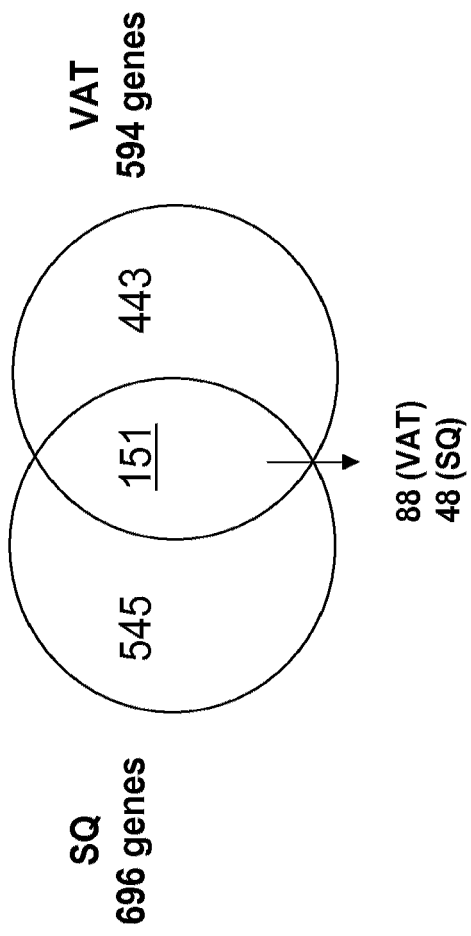
FIG. 1: Selection of critical adipose tissue regulatory genes. The Venn diagrams illustrate the selection of genes based on the following criteria. 1) Similar regulation by high fat feeding in subcutaneous (SCAT or Sq) and visceral (VAT). 151 genes were selected (48 for SCAT and 88 for VAT). 2)

Among those 151 genes, selection of genes regulated by Rimonabant treatment (14 for SCAT and 54 for VAT). This led to the selection of 34 genes regulated in both tissues by high fat feeding and Rimonabant. Among those genes, 16 have expression level correlated with body weight of L, M and H groups (obesity-linked) and 18 are regulated by HFD to the same level in each subgroup (not obesity-linked).

FIG. 2: Vgll3 expression in various tissue and cell types. mRNA levels of Vgll3 were measured by RT-PCR: A) in spleen, muscle (gastrocnemius), heart, lung, kidney, liver, brown adipose tissue (BAT), subcutaneous (SCAT) and visceral (VAT) adipose tissues. Results are expressed as relative levels compared to the liver expression set at 1. B) In SCAT and VAT of wild-type (white bar) and Ob/Ob mice (black bar) (n=5), p<0.05 data are shown as mean±sd and expressed as fold increase relative to the control SCAT set at 1. C) In SVF (black bar) and isolated adipocytes (white bar) of mice (n=5). Data are expressed as fold increase relative to SCAT SVF expression. D) In SCAT (black bar) and VAT (white bar) from human whole tissue, isolated adipocytes, isolated preadipocytes and adipocytes differentiated in vitro. Data are expressed as levels relative to whole tissue SCAT expression set arbitrary at 1. E) in 3T3-L1 cells prior DMI treatment day-2 and after DMI treatment until day 7. N=2-3 sets of cells. Data are represented as levels relative to the expression at day 0.

FIG. 3: Overexpression of Vgll3 cDNA in 3T3-L1 cell line. A) 3T3-L1 cells transduced with retroviruses expressing the human cDNA of Vgll3. Oil-red-O pictures of differentiated 3T3-L1 at day 10. B) aP2 (marker of differentiation) mRNA expression measured by RT-PCR in the same cells as in A) at day 10. Results are expressed as mean±sd P<0.005 n=3.

Material and Methods

Animals Treatment

C57BL/6J mice, which are obesity-prone (Collins et al. 2004), were fed for 6 months with a high fat diet (HFD). After 6 months of HFD, mice exhibited scattered body weights with various degrees of glucose intolerance (measured by a glucose tolerance test. The HFD mice were separated into 3 groups displaying the same level of glucose intolerance but with low (L), medium (M) or high (H) body weights and treated them, as well as normal chow (NC) fed mice, for one month with vehicle or rimonabant (10 mg·kg$^{-1}$·day$^{-1}$), to normalize their body weight.

RNA Preparation, Labelling and Hybridization on cDNA Microarrays.

RNA from 5 different mice per group was extracted from visceral and subcutaneous adipose tissues using pegGOLD Trifast™ (peqlab) and chloroform-isoamylalcool (24:1) extraction. RNA was precipitated with isopropanol and purified by passage over RNeasy columns (Qiagen). RNA quality was checked before and after amplification with a Bioanalyzer 2100 (Agilent). RNA was reverse transcribed and RNA was amplified with MessageAmp™ kit (Ambion). A Mouse Universal Reference (Clontech) was similarly amplified and both adipose tissue and reference RNAs were labeled by an indirect technique with Cy5 and Cy3 according to published protocols (De Fourmestraux et al., 2004). Labeled RNAs were hybridized to microarrays containing 17664 cDNAs prepared at the DNA Array Facility of the University of Lausanne. Scanning, image, and quality control analyses were performed as previously published (de Fourmestraux et al., 2004). Data were expressed as log$_2$ intensity ratios (Cy5/Cy3), normalized with a print tip locally weighted linear regression (Lowess) method and filtered based on spot quality and incomplete annotation. All analysis were performed with the R software for statistical computing available at the Comprehensive R Archive Network (cran.us.r-project.org/).

RNA Extraction and Real-Time PCR

Total RNA was isolated from cultured cells using peg-GOLD TriFast reagent according to the manufacturer's instructions (Axonlab). First strand cDNA was synthesized from 0.5 µg of total RNA using random primers and Superscript II (Invitrogen). Real time PCR was performed using Power SYBR Green Mix (Applied Biosystem). The following primers were used for mouse genes: SEQ ID NO.5 (Vgll3-Forward), SEQ ID NO.6 (Vgll3-Reverse), SEQ ID NO.9 (cyclophilin-Forward), SEQ ID NO.10 (cyclophilin-Reverse), SEQ ID NO.13 (aP2-Forward), SEQ ID NO.14 (aP2-Reverse). The following primers were used for human genes: SEQ ID NO.7 (hVgll3-Foward), SEQ ID NO.8 (hVgll3-Reverse), SEQ ID NO.11 (cyclophilin-Forward), SEQ ID NO.12 (cyclophilin-Reverse)

Isolation of Adipocytes and Stromal Vascular Fraction (SVF) from Adipose Tissue

Eights week-old male C57BL/6J mice (n=6-8) were euthanized by $CO_2$ inhalation and epididymal (visceral) and subcutaneous adipose tissue were collected and placed in DMEM medium containing 10 mg/mL fatty acid-poor BSA (Sigma-Aldrich, St. Louis, Mich.). The tissue was minced into fine pieces and then digested in 0.12 units/mL collagenase type I (Sigma) at 37° C. in a shaking water bath (80 Hz) for 1 hour. Samples were then filtered through a sterile 250 µm nylon mesh (Scrynel NY250HC, Milian) to remove undigested fragments. The resulting suspension was centrifuged at 1100 RPM for 10 min to separate SVF from adipocytes. Adipocytes were removed and washed with DMEM buffer. They were then suspended in pegGOLD TriFast reagent (Axonlab) and RNA was isolated according to the manufacturer's instructions. The SVF fraction was incubated in erythrocyte lysis buffer (0.154 mM $NH_4Cl$, 10 mM $KHCO_3$, 0.1 mM EDTA) for 2 min. Cells were then centrifuged at 1100 RPM for 10 min and re-suspended in 500 µl of pegGOLD TriFast reagent (Axonlab) for RNA isolation.

Cell Culture

3T3-L1 cells were cultured in DMEM (Gibco) with 10% FBS (Gibco) at 5% $CO_2$. After retroviral infection (see below), cells were allow to grow to confluence in either 100-mm or 60-mm dishes in DMEM with 10% FBS. Once confluence was reached, cells were exposed to differentiation medium containing dexamethasone (1 µM), insulin (5 µg/ml), and isobutylmethylxanthine (0.5 µM) (DMI). After 2 days cells were maintained in medium containing insulin (5 µg/ml) until ready for harvest at 7 days.

Oil-Red-O Staining

After 7 to 10 days of differentiation, cells were washed once in PBS and fixed with formaldehyde (Formalde-fresh; Fisher) for 15 minutes. The staining solution was prepared by dissolving 0.5 g oil-red-O in 100 ml of isopropanol; 60 ml of this solution was mixed with 40 ml of distilled water. After 1 hour at room temperature the staining solution was filtered and added to dishes for 4 hours. The staining solution was then removed and cells were washed twice with distilled water.

Generation of Retroviral Constructs and Retroviral Infections

Retroviruses were constructed in the RNAi-Ready pSI-REN-RetroQ ZsGreen (pSIREN Clontech) or pMSCV puromycin plasmid (pMSCV, Clontech). Viral constructs were transfected using calcium-phosphate method described in Jordan, M., et al. (2004) into 293 HEK packaging cells along with constructs encoding gag-pol and the VSV-G protein. Supernatants were harvested after 48 h in presence of 3 µm of Trichostatin A (Sigma) and either used immediately or snap frozen and stored at −80° C. for later use. Viral supernatants were added to the cells for 6 hours in the presence of polybrene (4 μg/ml) and diluted two times with fresh medium for the next 15 hours.

Overexpression Constructs

A modified pMSCV puromycin retroviral plasmid (from Clontech) expressing a GFP marker was used to over-expressed the cDNA of Vgll3 into cells. The cDNA (SEQ ID NO.15) was inserted blunted into the hpaI restriction site from the multicloning site of pMSCV. The resulting colonies were tested for the right orientation and selected by enzymes digestion. The right clone was selected and amplified and used for retroviral infection of 3T3-L1 cells.

Results

Example 1

Microarray Results

Figure 1B:
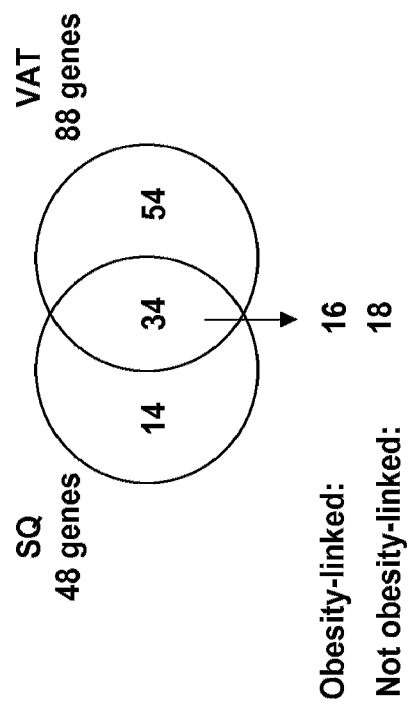

Bioinformatic analysis of the microarray data was performed to identify genes that fulfilled the three following criteria: (i) regulated by high fat feeding, (ii) similar regulated expression by high fat feeding in both visceral and subcutaneous fat and (iii) similar normalization of their expression by Rimonabant treatment (FIG. 1). Out of the ~17'000 gene targets present on the cDNA microarray used, 34 genes fulfilled these criteria, which are listed in Table 1. Remarkably, 10 of these genes—Cav1, Fgf1, Fndc3b, Kif5b, Mest, Npr3, Pik3ca, Sparc, Vldlr, and Wwtr1—were previously known to be important regulators of adipose tissue development and function. Some of these genes had expression levels correlated with body weight gain (shown in grey in Table 1), suggesting a potential role in hyperplasia and/or hypertrophy of adipose tissues during obesity. These results validate the approach used to identify possible novel targets for therapeutic treatment of obesity.

Most importantly, many of the genes cited in table 1 have never been studied in the context of in adipose tissue development or biology. These genes belong to the following classes of function: extracellular matrix/cell interaction, cytoskeleton, intracellular signalling, enzymes, and transcription factors/co-factors. They are likely involved in tissue remodelling, and particularly in adipocyte development. One of these genes, Vgll3 gene and its role in adipocyte biology, is presented herein and constitutes one aspect of the present invention.

The mouse and human sequences of Vgll3 as used in the present invention corresponds to SEQ ID NO.1 and NO.2 and SEQ ID NO.3 and NO.4 respectively.

TABLE 1

List of 34 gene candidates regulated by HFD and Rimonabant in SCAT and VAT.

| Gene name | Biological function and references |
|---|---|
| Acetyl-Coenzyme A dehydrogenase, medium chain (Acadm) | |
| ARP2 actin-related protein 2 homolog (Actr2) | |
| Amyloid beta (A4) precursor protein (App) | |
| Annexin A2 (Anxa2) | Role in actin-assembly |
| Calmodulin 1 (Calm1) | |
| Caveolin, caveolae protein 1 Cav1) | Role in lipid homeostasis |
| Cyclin G1 (Ccgn1) | |
| Cold shock domain containing E1 (Csde) | |
| Expressed sequence AW112037 | |
| Fibroblast growth factor 1 (Fgf1) | Regulator of human adipogenesis |
| Fibronectin type III domain containing 3B (Fndc3b) | Role in adipogenesis |
| Kinesin family member 5B (Kif5b) | Role in insulin-stimulated GLUT4 translocation to the plasma membrane |
| Mesoderm specific transcript (Mest) | Adipocyte differentiation and enlargement |
| Nucleosome assembly protein 1-like 1 (Nap1L1) | |
| Nidogen 1 (Nid1) | |
| natriuretic peptide receptor 3 (Npr3) | Possible role in sodium retention characteristic of obesity associated hypertension |
| nuclear undecaprenyl pyrophosphate synthase 1 homolog (Nus1) | |
| Phosphatidylinositol 3-kinase, catalytic, alpha polypeptide (Pik3ca) | Essential for proper growth factor signaling. Role in adipogenesis |
| Placenta-specific 8 (Plac8) | |
| Pleckstrin homology domain containing, family C (Plekhc1) | |
| Protein tyrosine phosphatase 4a1 (Ptp4a1) | Implicated in cell growth, differentiation, and tumor invasion |
| Related RAS viral (Rras2) oncogene homolog 2 | |
| Retinitis pigmentosa 9 homolog (Rp9h) | |
| Secreted acidic cysteine rich glycoprotein (Sparc) | Mediates cell-matrix interactions and play a differentiation and angiogenesis |
| Signal-induced proliferation-associated 1 like 1 (Sipa1L1) | |
| Spectrin beta 2 (Spnb2) | |
| ST3 beta-galactoside alpha-2,3-sialyltransferase 6 (St3gal6) | |
| Vestigial like 3 (Vgll3) | |
| Very low density lipoprotein receptor (Vldlr) | Involved in lipolysis |
| Zinc finger, DHHC domain containing 2 (Zdhhc2) | |
| WD repeat domain 26 (Wdr26) | |
| WW domain containing transcription regulator 1 (Wwtr1) | regulates mesenchymal stem cell differentiation |
| Expressed sequence AW112037 | |
| RIKEN cDNA B930093H17 gene (like-glycosyltransferase) | |

The full name and gene symbol are showed in the first column. The biological role for known genes and references are indicated in the second column. All these genes were up-regulated by HFD and normalized by Rimonabant treatment, excepted for Plac8 Rp9h, which were down-regulated by HFD. The genes correlated to body weight increase are shown in *italic*.

Example 2

Tissue and Cellular Expression of the Selected Genes

To better understand the role of Vgll3 in adipocytes development, its pattern of expression was first characterized. mRNA levels were measured by RT-PCR in various mouse tissues, in isolated preadipocytes and adipocytes, in visceral adipose tissue (VAT) and subcutaneous adipose tissue (SCAT) of mouse obesity model (Ob/Ob mice) and in human adipose tissues.

Vgll3 is highly expressed in kidney compared to other organs. It has a similar expression in VAT, SCAT, muscle and heart. The lowest expression is observed in liver, BAT and spleen. Vgll3 levels are normalized with cyclophilin A levels for each tissue and are expressed as relative fold increase compared to the liver level set arbitrarily at 1 (FIG. 2A).

Adipose tissue is a complex tissue that includes not only mature adipocytes, but also precursor cells such as preadipocytes as well as blood vessels, macrophages and fibroblastic cells. Based on a collagenase I digestion technique, stromal vascular fraction (SVF) (including preadipocyte, endothelial and macrophage cells) was separated from the isolated adipocyte fraction.

Figure 2B:
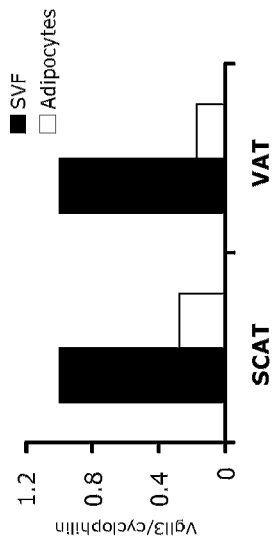

In white adipose tissues of Ob/Ob mice, Vgll3 levels are increased (FIG. 2B). The same expression patterns were observed in microarray studies.

Figure 2C:
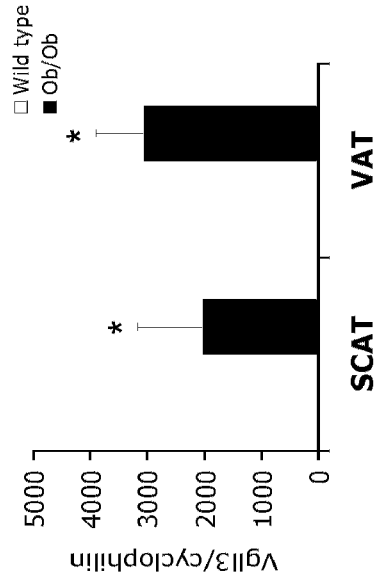

Adipose tissue is a complex tissue that includes not only mature adipocytes, but also precursor cells such as preadipocytes as well as blood vessels, macrophages and fibroblastic cells. Based on a collagenase I digestion technique, stromal vascular fraction (SVF) (including preadipocyte, endothelial and macrophage cells) was separated from the isolated adipocyte fraction. Vgll3 is predominantly expressed in the stromal vascular fraction, containing preadipocytes (FIG. 2C). These results indicate that Vgll3 might be involved in differentiation or proliferation processes.

Figure 2E:
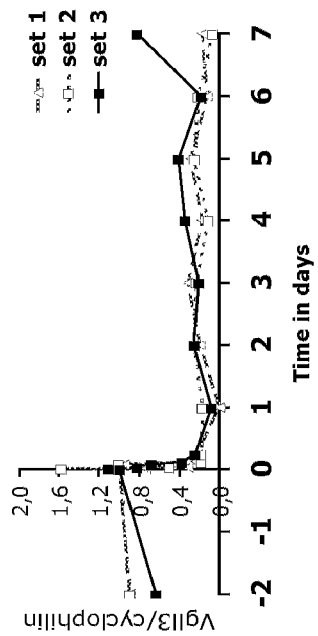
Figure 2D:
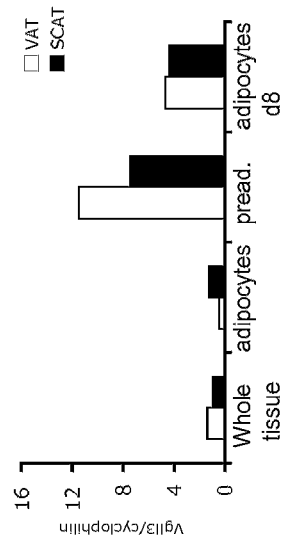

The next step was to determine whether Vgll3 gene is conserved among species. To address this question, a RT-PCR was performed on human adipose tissue samples. Preadipocytes and adipocytes were isolated from SCAT or VAT. Isolated preadipocytes were induced to differentiate in vitro until day 7. Results showed that Vgll3 is indeed expressed in human fat (FIG. 2D).

Altogether these results suggest that Vgll3 is a relevant candidate gene for adipocytes development, possibly required for adipogenesis or fat tissue enlargement in obesity since Vgll3 prevent these processes as it is strongly suppressed in adipose tissue of HFD and of Ob/Ob mice.

Example 3

Expression of Selected Genes During 3T3-L1 Differentiation

Next, the expression of Vgll3 gene was assessed during adipogenesis. For that purpose, mRNA levels were measured by RT-PCR during a detailed differentiation time-course of 3T3-L1 (an adipogenic cell line) (FIG. 2E). Interestingly, Vgll3 expression is decreased as soon as the DMI is added to the cells, and remains at very low levels during all 7 days, further suggesting that this gene is specifically down regulated to allow adipogenesis.

Example 4

Overexpression of Vgll3 in 3T3-L1 Cell Line Decrease Adipogenesis

Figure 3A:
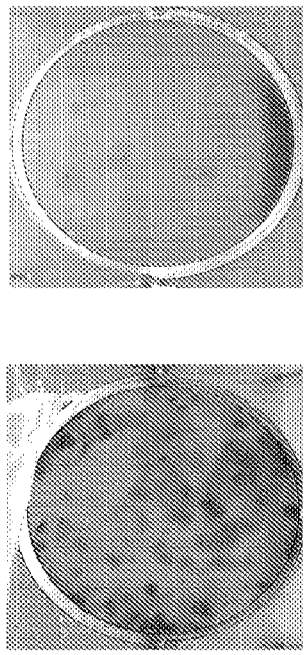
Figure 3B:
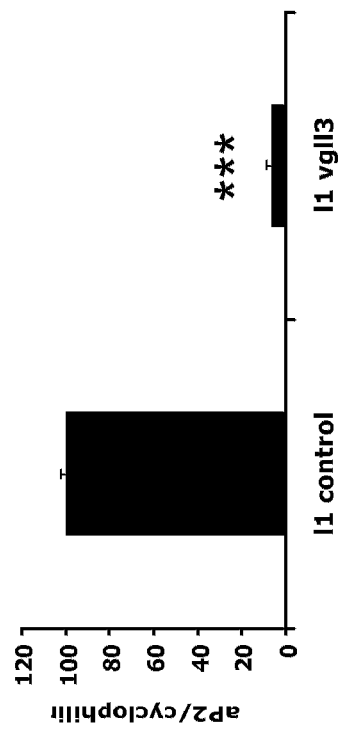

For the gain-of-function study, the cDNA of the human sequence of Vgll3 was subcloned into the pMSCV retroviral plasmid from Clontech. After infection, the 3T3-l1 cells were allowed to reach confluence and differentiated with DMI. At day 10, cells were stained for lipid content with oil-red-O (FIG. 3A). The overexpression of Vgll3 decreases the adipogenic potential of 3T3-L1. This result was confirmed by measuring the levels of aP2, an adipogenic marke, which is decreased by 90% in 3T3-L1 cells infected with retroviruses expressing Vgll3 (FIG. 3B).

BIBLIOGRAPHY

Banerjee, S. S., M. W. Feinberg, M. Watanabe, S. Gray, R. L. Haspel, D. J. Denkinger, R. Kawahara, H. Hauner, and M. K. Jain. 2003. The Kruppel-like factor KLF2 inhibits peroxisome proliferator-activated receptor-gamma expression and adipogenesis. J Biol. Chem. 278:2581-4. Epub 2002 Nov. 7.

Chen, H. H., T. Maeda, S. J. Mullett, and A. F. Stewart. 2004. Transcription cofactor Vgl-2 is required for skeletal muscle differentiation. Genesis 39:273-9. mechanisms. Cell Metab. 1:93-106.

Chen, Z., J. I. Torrens, A. Anand, B. M. Spiegelman, and J. M. Friedman. 2005. Krox20 stimulates adipogenesis via C/EBPbeta-dependent and -independent mechanisms. Cell Metab. (2):93-106.

Collins, S., T. L. Martin, R. S. Surwit, and J. Robidoux. 2004. Genetic vulnerability to diet-induced obesity in the C57BL/6J mouse: physiological and molecular characteristics. Physiol Behav 81:243-8.

De Fourmestraux V, Neubauer H, Poussin C, Farmer P, Falquet L, Burcelin R, Delorenzi M and Thorens B., 2004 Transcript profiling suggests that differential metabolic adaptation of mice to a high fat diet is associated with changes in liver to muscle lipid fluxes. J. Biol. Chem. 279:50743-53

Gray, S., M. W. Feinberg, S. Hull, C. T. Kuo, M. Watanabe, S. Sen-Banerjee, A. DePina, R. Haspel, and M. K. Jain. 2002. The Kruppel-like factor KLF15 regulates the insulin-sensitive glucose transporter GLUT4. J Biol Chem 277:34322-8.

Jimenez, M. A., P. Akerblad, M. Sigvardsson, and E. D. Rosen. 2007. Critical role for Ebf1 and Ebf2 in the adipogenic transcriptional cascade. Mol Cell Biol 27:743-57.

Kang, S., C. N. Bennett, I. Gerin, L. A. Rapp, K. D. Hankenson, and O. A. Macdougald. 2007. Wnt signaling stimulates osteoblastogenesis of mesenchymal precursors by suppressing CCAAT/enhancer-binding protein alpha and peroxisome proliferator-activated receptor gamma. J Biol Chem 282:14515-24.

Paumard-Rigal, S., A. Zider, P. Vaudin, and J. Silber. 1998. Specific interactions between vestigial and scalloped are required to promote wing tissue proliferation in *Drosophila melanogaster*. Dev Genes Evol 208:440-6.

Rosen, E. D., C. H. Hsu, X. Wang, S. Sakai, M. W. Freeman, F. J. Gonzalez, and B. M. Spiegelman. 2002. C/EBPalpha induces adipogenesis through PPARgamma: a unified pathway. Genes Dev 16:22-6.

Soubrier F, Cameron B, Manse B, Somarriba S, Dubertret C, Jaslin G, Jung G, Caer CL, Dang D, Mouvault J M, Scherman D, Mayaux J F and Crouzet J. 1999. pCOR: a new design of plasmid vectors for nonviral gene therapy. Gene Ther. August; 6(8):1482-8.

The invention claimed is:

1. A method for reducing differentiation of mesenchymal precursor cells into mature adipocytes in a patient in need thereof comprising delivering to a mesenchymal precursor cell a recombinant expression vector comprising a nucleotide sequence encoding a Vestigial-like 3 factor (Vgll3) protein functionally linked to a regulatory sequence wherein overexpression of the recombinant Vgll3 protein relative to endogenous levels of Vgll3 in a control mesenchymal cell reduces differentiation of the mechenchymal precursor cell into a mature adipocyte.

2. The method of claim 1, wherein reduced differentiation of mechenchymal precursor cells into mature adipocytes results in reduced adipogenesis.

3. The method of claim 1, wherein the vector comprises the nucleic acid sequence selected from the group consisting of SEQ ID NO:1, SEQ ID NO: 3 and SEQ ID NO: 15.

4. The method of claim 1, wherein the Vgll3 recombinant protein comprises the amino acid sequence of SEQ ID NO:2 or SEQ ID NO:4.

5. The method of claim 2, wherein the patient suffers from a disorder selected from the group consisting of: obesity, hypertension, coronary artery disease, dyslipidemia, insulin resistance, type 2 diabetes, cardiovascular disorders and metabolic syndrome.

6. The method of claim 1, wherein the vector comprises a promoter comprising the nucleic acid sequence of SEQ ID NO: 17.

7. The method of claim 2, wherein the reduction in adipogenesis results in a reduction in visceral fat accumulation, subcutaneous fat accumulation, or both visceral and subcutaneous fat accumulation.

8. The method of claim 2, wherein the reduction in adipogenesis results in a reduction in obesity.

* * * * *

SEQUENCE LISTING

<160> NUMBER OF SEQ ID NOS: 18

<210> SEQ ID NO 1
<211> LENGTH: 3334
<212> TYPE: DNA
<213> ORGANISM: Mus musculus
<220> FEATURE:
<221> NAME/KEY: CDS
<222> LOCATION: (1)..(981)

<400> SEQUENCE: 1

```
atg agt tgt gcg gag gtg atg tat cac ccc cag ccg tat gga gcg ccc      48
Met Ser Cys Ala Glu Val Met Tyr His Pro Gln Pro Tyr Gly Ala Pro
1               5                  10                  15 cag tat ctg ccc aac cct gtg gca gct gca acc tgc cct aca gcc tgc      96
Gln Tyr Leu Pro Asn Pro Val Ala Ala Ala Thr Cys Pro Thr Ala Cys
            20                  25                  30 tat cat ccg gct ccc caa cct ggc cag cag aag aag tta gcg gta tac     144
Tyr His Pro Ala Pro Gln Pro Gly Gln Gln Lys Lys Leu Ala Val Tyr
        35                  40                  45 agc aag atg cag gac tct ctg gaa gtc acg ctt ccc agc aaa caa gag     192
Ser Lys Met Gln Asp Ser Leu Glu Val Thr Leu Pro Ser Lys Gln Glu
    50                  55                  60 gag gag gag gag gag gag gag gat gag gag gag gag gag aaa gac cag     240
Glu Glu Glu Glu Glu Glu Glu Asp Glu Glu Glu Glu Glu Lys Asp Gln
65                  70                  75                  80 cct gcc gag atg gag tac ctt aac tct cgc tgt gtc ctt ttc act tat     288
Pro Ala Glu Met Glu Tyr Leu Asn Ser Arg Cys Val Leu Phe Thr Tyr
                85                  90                  95 ttc cag gga gac att ggg tca gta gtg gat gaa cac ttc tca aga gct     336
Phe Gln Gly Asp Ile Gly Ser Val Val Asp Glu His Phe Ser Arg Ala
            100                 105                 110 ttg ggc caa gcc aac acc ttg cat ccc gaa tct gcc att tca aaa agc     384
Leu Gly Gln Ala Asn Thr Leu His Pro Glu Ser Ala Ile Ser Lys Ser
        115                 120                 125 aag atg ggg cta acc ccc cta tgg cga gac agc tca gct ctt tcg agc     432
Lys Met Gly Leu Thr Pro Leu Trp Arg Asp Ser Ser Ala Leu Ser Ser
    130                 135                 140 cag cgg agt aat ttt cca act tcc ttt tgg acc agc tct tac caa ccc     480
Gln Arg Ser Asn Phe Pro Thr Ser Phe Trp Thr Ser Ser Tyr Gln Pro
145                 150                 155                 160 cca ccc gcg cct tgt ttg ggg gga gtt cat cct gac ttc caa gtc act     528
Pro Pro Ala Pro Cys Leu Gly Gly Val His Pro Asp Phe Gln Val Thr
                165                 170                 175 gca ccc cac ggc acc ttt act aca gca gat ccc aac tct tgg cca gga     576
Ala Pro His Gly Thr Phe Thr Thr Ala Asp Pro Asn Ser Trp Pro Gly
            180                 185                 190 cat ggc ctg cat cag act ggc ccc gcc cca ccc cct acg gcg tct gag     624
His Gly Leu His Gln Thr Gly Pro Ala Pro Pro Pro Thr Ala Ser Glu
        195                 200                 205 tct tgg cac tat cct ctg gca tct cag gtg agc ccg tcc tac agc cac     672
Ser Trp His Tyr Pro Leu Ala Ser Gln Val Ser Pro Ser Tyr Ser His
    210                 215                 220 atg cat gac atg tac ctg cgc cat cat cac cct cac gct cac gtg cac     720
Met His Asp Met Tyr Leu Arg His His His Pro His Ala His Val His
225                 230                 235                 240 cat cgc cac cac cac cac cac cac cca act gct ggc tct gcc ttg gat     768
His Arg His His His His His His Pro Thr Ala Gly Ser Ala Leu Asp
                245                 250                 255 ccc gcc tat ggc cac ctg cta atg cca tca gtg cga gct gcc agg att     816
Pro Ala Tyr Gly His Leu Leu Met Pro Ser Val Arg Ala Ala Arg Ile
```

```
                  260               265               270
cct gct ccc cag tgc gac atc acc aag aca gat ctg act aca gtc acc      864
Pro Ala Pro Gln Cys Asp Ile Thr Lys Thr Asp Leu Thr Thr Val Thr
        275                 280                 285 acg gct acc tca gca tgg gcc gga gcc ttt cat ggg aca gtg gac atc      912
Thr Ala Thr Ser Ala Trp Ala Gly Ala Phe His Gly Thr Val Asp Ile
    290                 295                 300 gtg cca agt gtg ggc ttc gat aca ggt ctt cag cat cag gac aag agc      960
Val Pro Ser Val Gly Phe Asp Thr Gly Leu Gln His Gln Asp Lys Ser
305                 310                 315                 320 aaa gaa tca act tgg tac tga agcatggtat cagcagatca tatggcagca        1011
Lys Glu Ser Thr Trp Tyr
                325 tgaatccaag agcccactgg gaaaagatgc cattgggata tcccatccag aaatgggaca   1071 caggaaatgt ggagtgagaa gagaacatag aaggccattg tctttcgatt gaaccttttt   1131 ctggagaaaa catagagggc tctcctagtc cttgaggaag agcctttggg tttcttttcc   1191 ctcatctgag cctttgtcat ctgtgcaacg tcttgtttta cttgccttgt accagtacct   1251 gggctagctt ttgtatgcct tttattttt cttttttgaac cagtaacctt gtaaaaagat   1311 gatctaccaa atgaaaatgc tcatttcttc aggaaaaact attaactcca tcttcatcta   1371 tttttataga aatacaaaat ggttggttta gcatggaggg gatattttttg aagatgtaat   1431 ttttttttta atgttgtaac agtcgttgag ttctgtttaa agaacttgct ctcagaaaag   1491 cactggccaa aatgctgaag cgctgatcca tctttagagt ctgtgatgcg ctgtgtctgt   1551 gcttccgagg gtacctcaag ggtttcatcc ttcctccaac agtggcactg ccgtagacaa   1611 accctgcaac attgtgttca tgttgaaact cagtgaagac ttaattcgat gatagctctc   1671 ttagtttgct gttatatatg tctgtgcatc ttgaaagggg catttttcctt taaagggaca   1731 caaagggaag gggacttctc cgaaatagtt cttggaggtt gactaacaag aaaaaaattg   1791 gttaatgaac aatacttctc tatatagtcc agcttatctt aacatttagg tggagagctt   1851 acacatggct tcaaaatagg gaaaaaaaaa tcaatgcatt tagccatgat aactgtggac   1911 atcacggctg aattttccta atttctaacc attcgttcat ggatgacttt ggatgactgt   1971 gttttctgaa tacaaatgag tagtatcagg aaaggaagga gacacgtgtc aaaatgctga   2031 ctgttcctca tctttgtaaa agtgatgtat tctttatgca atgttttcac ttgatcattt   2091 ttgcaagatt ttcatttgct tttaagtgta attagtttct aaaaaattag agcaaaataa   2151 aagtggtaat ggatttaagt ttatgcttca attacacaaa ctggttgaaa gactcaaagc   2211 ttgagaaatg aacttaacat ggcccacaag ataaaaaaaa tgaagttgga attaacttta   2271 agagaaaatt ggacaaagtt tgggattatg aaggtagcga tgagtggcaa gtcaaagaca   2331 caacctattt tttcctttta gttgctccca gccacacagg gcattagtgt agtatagatg   2391 cttttatttta ataatgtttc tcaaattctt ccattcttct caggccacac aaaacagaag   2451 gttaagtcac gtgctatgtt ctgtttttaa ttgtgaactt catgggtgag aatatttttac   2511 acattaacaa cacaacaagc agctacacag aattctcaca actcatttcc aaacatttca   2571 cttggctgta tcttagacat tcgtttctct tcctgctgtg ttttgaatta taaacccact   2631 tcatctcttg tagtcacaga ctcccatcat tttttttcatc ttgatttttc tttaacacag   2691 tcttcacatt tttatcaata taatctagac ttaaggaagc tcccactcac cagtttagga   2751 actttagcat ccagataatg ggcctcatta aattctgtgc atatttatct ggattttgat   2811 aacatataaa gttgttttat ttgttatctg tatctgcata aatatgtgga gcatagagtt   2871
```

```
gaatgaatct atcaaattca tgatgtcttg agtcttctta agttgtaaga attgagtact    2931
tagcaactct catgagggaa acactttggc tgttgtcaca tccttccttg agatatatta    2991
acttgcattg ccgtgtctct tagaacagta ccacacttcc aatcactgag ctcactccat    3051 taatttttc cagataaggg aggataagag gactaacttg ttttctttcc ttatttacca    3111
tcattctgga ttgaaaatga aagtagttaa tttcgtggtt ttgctgtgat atccttgtaa    3171
ctatggccaa acatgatttt ggttcaagat caaaggaaag tgaagaatct gaattctatt    3231
gcatgcaaca tgcaacatgc tctctcttta agaacaggca taggtatcag tggcacattg    3291
tcatcaaagg aggagaccaa aatctaataa aaggaaaaag aac                      3334
```

<210> SEQ ID NO 2
<211> LENGTH: 326
<212> TYPE: PRT
<213> ORGANISM: Mus musculus

<400> SEQUENCE: 2

```
Met Ser Cys Ala Glu Val Met Tyr His Pro Gln Pro Tyr Gly Ala Pro
1               5                   10                  15

Gln Tyr Leu Pro Asn Pro Val Ala Ala Thr Cys Pro Thr Ala Cys
            20                  25                  30

Tyr His Pro Ala Pro Gln Pro Gly Gln Gln Lys Lys Leu Ala Val Tyr
        35                  40                  45

Ser Lys Met Gln Asp Ser Leu Glu Val Thr Leu Pro Ser Lys Gln Glu
    50                  55                  60

Glu Glu Glu Glu Glu Glu Asp Glu Glu Glu Lys Asp Gln
65                  70                  75                  80

Pro Ala Glu Met Glu Tyr Leu Asn Ser Arg Cys Val Leu Phe Thr Tyr
                85                  90                  95

Phe Gln Gly Asp Ile Gly Ser Val Val Asp Glu His Phe Ser Arg Ala
            100                 105                 110

Leu Gly Gln Ala Asn Thr Leu His Pro Glu Ser Ala Ile Ser Lys Ser
        115                 120                 125

Lys Met Gly Leu Thr Pro Leu Trp Arg Asp Ser Ala Leu Ser Ser
    130                 135                 140

Gln Arg Ser Asn Phe Pro Thr Ser Phe Trp Thr Ser Tyr Gln Pro
145                 150                 155                 160

Pro Pro Ala Pro Cys Leu Gly Gly Val His Pro Asp Phe Gln Val Thr
                165                 170                 175

Ala Pro His Gly Thr Phe Thr Ala Asp Pro Asn Ser Trp Pro Gly
            180                 185                 190

His Gly Leu His Gln Thr Gly Pro Ala Pro Pro Thr Ala Ser Glu
        195                 200                 205

Ser Trp His Tyr Pro Leu Ala Ser Gln Val Ser Pro Ser Tyr Ser His
    210                 215                 220

Met His Asp Met Tyr Leu Arg His His His Pro His Ala His Val His
225                 230                 235                 240

His Arg His His His His His His Pro Thr Ala Gly Ser Ala Leu Asp
                245                 250                 255

Pro Ala Tyr Gly His Leu Leu Met Pro Ser Val Arg Ala Ala Arg Ile
            260                 265                 270

Pro Ala Pro Gln Cys Asp Ile Thr Lys Thr Asp Leu Thr Thr Val Thr
        275                 280                 285
```

```
Thr Ala Thr Ser Ala Trp Ala Gly Ala Phe His Gly Thr Val Asp Ile
    290             295                 300
Val Pro Ser Val Gly Phe Asp Thr Gly Leu Gln His Gln Asp Lys Ser
305             310                 315                 320
Lys Glu Ser Thr Trp Tyr
                325

<210> SEQ ID NO 3
<211> LENGTH: 10396
<212> TYPE: DNA
<213> ORGANISM: Homo sapiens
<220> FEATURE:
<221> NAME/KEY: CDS
<222> LOCATION: (365)..(1345)

<400> SEQUENCE: 3
cgggcctggg ctgtggctgt gactggcgct gccgtgggcg ccgcagccct cgcgggagcc      60
ggacgcggta atgccccagc ggcgcagcgg gcggctgcgt ccctgagccg ctatataagc     120
gcggcaggga acatccggag gggctgaaga tgaaggtgcc cgcgcatggg cccccgctga     180
ttgccagtcc ctcccgaccc cgcgccccgc gcggagcccg aggccgccga ggacccgcct     240
tcgccgcagt agcagctgga gcagcgacag aggcggcagc tgcggcggcg gcggcgcccg     300 cgccctcgc gccagcgcgt agagcggcgg cggcagctcg ggggccgcca ctgccccggc     360 tgcc atg agt tgt gcg gag gtg atg tat cac ccc cag cct tat gga gcg    409
     Met Ser Cys Ala Glu Val Met Tyr His Pro Gln Pro Tyr Gly Ala
     1               5                   10                  15 tcc cag tat ctg ccc aac ccc atg gca gcg aca acc tgc ccc aca gcc    457
Ser Gln Tyr Leu Pro Asn Pro Met Ala Ala Thr Thr Cys Pro Thr Ala
                20                  25                  30 tac tat cag ccg gcg ccc caa cct ggc cag cag aag aag tta gcg gta    505
Tyr Tyr Gln Pro Ala Pro Gln Pro Gly Gln Gln Lys Lys Leu Ala Val
             35                  40                  45 ttc agc aag atg cag gac tct ctg gaa gtc acc ctt ccc agc aaa caa    553
Phe Ser Lys Met Gln Asp Ser Leu Glu Val Thr Leu Pro Ser Lys Gln
         50                  55                  60 gag gag gag gat gag gag gag gag gag gag gag aaa gac cag cct gcc    601
Glu Glu Glu Asp Glu Glu Glu Glu Glu Glu Glu Lys Asp Gln Pro Ala
     65                  70                  75 gag atg gag tac ctt aac tct cgc tgt gtc ctt ttc act tat ttc cag    649
Glu Met Glu Tyr Leu Asn Ser Arg Cys Val Leu Phe Thr Tyr Phe Gln
80                  85                  90                  95 gga gac att ggg tca gta gtg gat gaa cac ttc tca aga gct ttg ggc    697
Gly Asp Ile Gly Ser Val Val Asp Glu His Phe Ser Arg Ala Leu Gly
                100                 105                 110 caa gcc atc acc ctc cat cca gaa tct gcc att tca aaa agc aag atg    745
Gln Ala Ile Thr Leu His Pro Glu Ser Ala Ile Ser Lys Ser Lys Met
            115                 120                 125 ggg cta acc ccc tta tgg cga gac agc tca gct ctc tca agc cag cgg    793
Gly Leu Thr Pro Leu Trp Arg Asp Ser Ser Ala Leu Ser Ser Gln Arg
        130                 135                 140 aat agt ttc cca act tcc ttt tgg acc agc tct tac cag ccc cca cct    841
Asn Ser Phe Pro Thr Ser Phe Trp Thr Ser Ser Tyr Gln Pro Pro Pro
145                 150                 155 gca cct tgt ttg ggg gga gtt cat cct gac ttc cag gtc act gga ccc    889
Ala Pro Cys Leu Gly Gly Val His Pro Asp Phe Gln Val Thr Gly Pro
160                 165                 170                 175 cct ggc acc ttt tct gca gct gat ccc agt cct tgg ccg gga cac aac    937
Pro Gly Thr Phe Ser Ala Ala Asp Pro Ser Pro Trp Pro Gly His Asn
                180                 185                 190
```

| | | |
|---|---|---|
| ctg cat cag act ggc cca gcc cct ccc cct gct gtg tct gag tcc tgg<br>Leu His Gln Thr Gly Pro Ala Pro Pro Pro Ala Val Ser Glu Ser Trp<br>                195                          200                        205 | | 985 |
| cct tat cct ttg aca tct cag gtg agc cca tcc tac agc cat atg cat<br>Pro Tyr Pro Leu Thr Ser Gln Val Ser Pro Ser Tyr Ser His Met His<br>                210                          215                        220 | | 1033 |
| gac gtg tac atg cgg cac cac cac cct cat gcc cac atg cac cac cgc<br>Asp Val Tyr Met Arg His His His Pro His Ala His Met His His Arg<br>            225                          230                        235 | | 1081 |
| cac cgc cac cat cat cac cat cac cac cct cct gct ggc tct gcc ctg<br>His Arg His His His His His His His Pro Pro Ala Gly Ser Ala Leu<br>240                          245                          250                        255 | | 1129 |
| gat cca tcc tat ggg cct ctg ctg atg cct tca gtg cat gcg gcc agg<br>Asp Pro Ser Tyr Gly Pro Leu Leu Met Pro Ser Val His Ala Ala Arg<br>                    260                          265                        270 | | 1177 |
| att cct gct ccc cag tgt gac atc aca aag aca gaa cca act aca gtc<br>Ile Pro Ala Pro Gln Cys Asp Ile Thr Lys Thr Glu Pro Thr Thr Val<br>                    275                          280                        285 | | 1225 |
| acc tct gct acc tca gca tgg gct gga gcc ttt cat gga aca gta gac<br>Thr Ser Ala Thr Ser Ala Trp Ala Gly Ala Phe His Gly Thr Val Asp<br>            290                          295                        300 | | 1273 |
| ata gtg ccc agc gtg gga ttc gat aca ggt cta cag cat caa gac aag<br>Ile Val Pro Ser Val Gly Phe Asp Thr Gly Leu Gln His Gln Asp Lys<br>305                          310                          315 | | 1321 |
| agt aag gaa tca ccg tgg tac tga aacacacaat cttagtgagt taagttgcag<br>Ser Lys Glu Ser Pro Trp Tyr<br>320                      325 | | 1375 |
| cataaatcca agggcccact gggaaaagat actgtcgggt ttttccattc agcaatagga | | 1435 |
| cacgaaaggc atagaaggag aagacaaagt gtcacgcagt tgactggttt tcggcctttc | | 1495 |
| ttgagaaagc aaagtgggtc ccagacattg aagaaaagca ttttatttg tttatttcct | | 1555 |
| catctgagcc tttgccaact gtgcaactct ctccttttgt tatcttgctt ttatcaatat | | 1615 |
| atagctaagt ttttgtttca ttttgatttt ttttttagc caaccacctt gtcaggaaag | | 1675 |
| gatgaaccac acattaaaat gttcattctt tcaggaatac aagtttgtag ctctatgtgc | | 1735 |
| atctattttt gtagaaatac aaaaagtttg gtttagcatt gatgggctat ttttgaggga | | 1795 |
| tgtatttttt ttaaaattgt aaaaattgtt gagttctgtt taagaactt gctctcagag | | 1855 |
| aagcactggc aaaaatgttt aaaatgctta tctctaagat gtctattata tgctctgtct | | 1915 |
| gtgctttcta ggttacctca aatgttttgt ttttttcctt cttacaaaag tagctatacc | | 1975 |
| gtagtcaaac caatgcagta ttgttttac attgaatctc agtaaagatt taattccatg | | 2035 |
| ctagctcaat tagttttgaa ttatatgtat agcttgaaaa gttttttttt aatgactgtg | | 2095 |
| ctaaagaaat gatattttat tgctttgatt tctcccaaag aataacttgg aggttgacta | | 2155 |
| ataagaaagt tggcataaac tttcaatcaa atgaagagtt tgcctagagg agactaattc | | 2215 |
| tctttctagc ccatccaaat ttgataaatg gaaccagagg ttatatacaa ctacaaggaa | | 2275 |
| aaaaatgcat ttaaccatgc cacctatgag tgccagtgac ttatttact tgttttaat | | 2335 |
| tattcattca tggcaattta aaagtcata ttaagtgg gattgtttt tcctgaaggg | | 2395 |
| catttgaagg aacaatatct gggaaggtac tagagaaatt acaaagcccg agctctttct | | 2455 |
| tataatgcca cctatccctg taagctaaac aaacaaacaa acaaacaaac aaacagttct | | 2515 |
| atatataata gttcaacaac agaacttaac aagtctcttt ttttgtttgt ttaaatctgg | | 2575 |
| ctttacttga tttaattcct ttttagaaag aaatttaggg caaaataaag tgtatattag | | 2635 |

```
gatttaaatt tatgccacaa tttaaaaata aaaccagagg ttatatacaa tttaaattgg     2695
gctaaaaatt aaaaatttga ggatttaact tgatatagct ctcaggatct aaataaagtt     2755
taaattatca ttaagacact gctaggagaa gattaagatt atgaaagtaa cagttattga     2815
tactgctgga cttcaaaggc aaagttcatt tcttccatta actgcttcca gagatgtcat     2875
gtaaaaaagt tagtgtatta gagaagtttt ttagctttat aaagaggttt tttcaaattt     2935
ctcccatttt tctctccacc cacataaaat agtatgttca gtgaaatgcc actttctatc     2995
tttaattgtt cgtatcatat atgcgaactt tttagacatg aacatgacat gttcagctag     3055
gcagagttct catagataat tttcaaatat tttccttggc tgtaatttat gtattcattt     3115
atatcctatc cgtcttttga gcttcagatc tatatactct tttgtactct catcactccg     3175
cactttgctg tttcttacct agactctctt ttacacaata tgcacatttt taccattgtg     3235
gggtccaaat ttaagatacc ttccactcac taataatatg aacttatatt tcctgggagt     3295
agccaggtta aattttctat actttggtcc ataatttgat ttgatatgat tgtttcattt     3355
ataatttgcc caaatacatg gagcacaaaa tttagtgaat ttataaatct ggatttgcct     3415
tgtgtccttc tgagttttca aaggcaagta ttcaacagtc cctgtgtgat gactgacagg     3475
gttatttgcc tcatccacat ccaccttcgg aatacattaa cttcctttgt aatttatttg     3535
aaagtagtgt taaactcatt cagatcattc agttggattt tcccaatgaa gaggaaaagg     3595
aaagtagtta ttcctagctc catttcttat tttccaccaa atttaattga agggcattaa     3655
ttagatgtct tcaccctgaa tttagacttt gctctgtgtt ctcccggtaa ctgtcagaca     3715
aaaagtttat tggctctgag gaactgagaa atgttgggaa cctggtttct gctgtacaca     3775
ggaaagattt gtaagtgagc tctctctttg aaaacaggac ccaggctggg cacagcagct     3835
catgcctgta atcctagtat tataggaggc agaggctcgg gaggattgct tgagcccagg     3895
agttcaagat cagcctaggc aacatgggga gaccctatcc ctacaaaaaa tttctgaaaa     3955
attacctggg cattgtgggg cacacctgtt gtcccagcta ctctggaggc tgagtccgga     4015
ggaacgtttg agcctgggag tttgagtttg cagcttgcag tgagctgtga ttgcaccact     4075
gtactccagc ttgggcaaca gagcaagatc ctgtctcaaa aggaaaaaga aaacaggacc     4135
taggtgtttg gggtacactg ccacccaggg agtggatcaa aaatatacat agaaagagaa     4195
tgagcatgtc tctataattg tcttctagga ccatattgct gttagaagtc ctaaaagagg     4255
atgggttgta atttagcata atattctgaa ttcattccaa gtttaaaatc ctgtcattct     4315
ctggctcttc ttttttcaca tcaaaatgat gctgttggac ttagaggctt ccgaactgtt     4375
ttattgaggg ctactatctg cctccacaat tttattaaaa ccactccacc tttagacaaa     4435
ggtgactttt gtctgatttt acaaatcaga ttttattcaa gctttctaaa tatctgtgaa     4495
gtagaccctg aaaattgtc tcgtttattt taaatagaat ctatgcttcc accaataaac     4555
catcgggagc taagaaacaa cataatgttg acaaatcagg aacctaacag attattttgt     4615
ctctcattat taatttgaaa gagcctctaa acttttgaga aatcaatgtg tcttcttaag     4675
aaagttaagc accctctctt aacttteece tctatttgct ctccttttte tttcttctta     4735 agagtattta tattattttg ttaagcaaaa atggctaaga ttgctctaaa atttgcaaaa     4795
tgaggagtgg attgcaaata attgagggat ttatttcttt aactttataa gactttaaaa     4855
aaaaaaccca aattctaagc actgacatga aagttgcctt tgagaagctt gttattcatt     4915
atacaaaaag tatttgccca ttcctattct aagatttgca gaatatgtca ccctatctag     4975
cttttgagtt tgctatctgg tttaatgttg tatttataat ttaaagtgga aatcagaaac     5035
```

```
tgtttcaaga acctgtattc tattccttac tgagtgtccc ttctttaaat agtgtttgct    5095
gaattaagcc gatgggggca gtggcgttaa gtggtggaaa aaggaaagta tatatgttag    5155
agttttgaat gagggataaa tagaaagcag aatgaattaa tggaaaagaa ctcggctgtt    5215
aggccattct ctaaattcta gtttagccaa aagtttatgt gtggtttggg gcttcattta    5275
tttatctcat gagtaaaatg gaataatacc taacaggcag gctctggaag ttggaaatca    5335
catacacaca cacacacaca cagacacaca cacacacgat caatcatgta gctcatatta    5395
gatgttcaat aaataacagc tactacagat gcctatcagt tgagtaagta gttcattaaa    5455
ttgagctccc aaaggtctct tctcttcaca tccatatccg tttctgcagc aatcaaatag    5515
atacatgatt gttttttctgt aagaaattac tgcaaagaga atcttttttct cctactaact    5575 gttccttcta cctggtatag gagataaatg tacgtttctt aattagctga cttttttagta    5635 tgtcatttct gaaggaaaaa taaattaacc ttaaagtggc atgtaggtcc aattcagttt    5695
tcctacatgt tccaaaattt tatttaaatt actgtgtcca aaattatgag gacagtgtca    5755
ttcattcacc atagtttata ttttttagtta tatatcaaac ttccttggca cctaggataa    5815
gaacatttct tttgaagtta tccaattttt ttttattttt acttgacttg aaggaaagtt    5875
ggaaaatatg gtggaaaaaa tcttccgcat taaaaggggg aaaaacacaa ccatttacga    5935
tctcagtcag cagatttact ctactcaagg aaaaaaagaa acaatcttat tggaagcaga    5995
tgttgacact gtgtcagtta ttgaagacgg aaggagttca cttgagccat tgcagttaca    6055 aagggggtatt gatggcagtt tggattcctg attgatcacc tttgcagcca agggaaagac    6115
agcagaaact gtatgggatc agaaatgaaa tcagcctgcc agtttaatgg agaggctcct    6175
agaaactcat ttttttttctt tcctgtaaga taaaagacat ctttcagaat aagaaaggct    6235
tgtttgagag agaaattaca gttattctc tgaaaatatt taaaggccaa agtgcccttt    6295
aaatctatta ttaaagcatt gaaactgtta ttaaaatcat tatagaaaaa ttaggtaaaa    6355
attttagcct aactttcaac atccattcaa aaacgaatgt tgaaaacaaa catataaccct    6415 ataaaaaagt gaatggctct ggcaagtggg ggcatgggtg gagtccataa ggaaacctca    6475
gtctcaataa cttcaaaatg ttactttttca tggtaacttg gtcatggaga ttggtcacag    6535
cacagacatt tagaatttt tagcaggttt tttttttctt ttgaatcttg tagtgctctc    6595
tgggaattgc accatgtaca cttttacaac ctacagaaat cgtcattatt gttaaagtat    6655
ctcaactttt ctatttcttt tattgtctat tgtgcttttt tgtttaaaaa tacttttata    6715
gttttaaagt attggtcaaa gtagtattct cttgaagttc tagtcaattt aatttgatcc    6775
aataagtttt tctgaatctc cttttttaagt tccaagaaat tctattataa ataagtgtac    6835
ttttaccaat tccattgtat aagcaaacag acacctttta gaaaaggata agtaatcatc    6895 aatttgttt tttaaaaaaa aaacaatttt ctagactact aaatttggca taagaataat    6955
tcttttaaaa tgcaacatac tttaattagt tttttggta tatgcataag atgtgaactt    7015
tcctattgat atcactttat attaatagag atgtacattt ctttctatgc cgtggctaga    7075 gcaaagtta ataatgatta tttacacaat tgatttaatt tcttaggata tgtataaatat    7135 tggatattat atctgattta aaaatactat tccatacatt ttttttttca ggagataaaa    7195
catagggaaa ggttttcatg tgaattcttt gtatcacttt gaagtacata tatttaaagg    7255
gaagatggat acaatttgtt tttattatat aaatctaggt aaggtgaaat gcttttgtca    7315
acaaaaatac agtgtagtga attttatatt tgtcacttga ttaggtaaac tgaaaactaa    7375
```

```
caatagaaat attattttac tgcattgaaa taccatgaac tttcagactt gttagttcta      7435
caagaagttg tgctacctta attttgtgtt tccagaaata aaaattaacc ttagttatgc      7495 tgtcatttttt aactaataaa aaaagtataa ttcataaaac ttttggcttt ataagataat     7555
tataaaatta tatattttt tctgttttg tggggttggg aaaacatttt cttatttcta       7615
ttcactcttc aaatgcaggt ctcataatat gtgtcaatga tataagatga tggaagactt     7675
tgtaataaaa acatatgtca ttatcttcaa tttgttcaat aaataattta atgtgaattg     7735
aatgtttgta ttttaacata gcatttggat ttggtctgca tttcttgaga atttaaagct    7795 cttttttgttt cctccttatt caattaagca tcttataaat attttggaaa ttacaacatc  7855
ttaggtgtta ttaattaaga agttaatttc tagggccaag aagtctatat gttacagcaa   7915
ggaatagatt ataaaataca tgtttataat ggaaaagaaa atgaaatggg gtatattaat   7975
tacataacag caagagtctt gagaaattta taatacaatg cttctaagga tattggttga  8035
ccaaggtgta ttttattgtt tttacatttg ttgacaggga ctctgccata agtagtatga   8095
aaaaacaaac aaaaacttt ctacgattca ttaacattga aaagagaatt ccaagacctt    8155
gtattctgaa gaaagctaga gtttctctaa gtgggccttc aattttctta ttacacgtat   8215
ctttaatgtg aaagtactaa agtctgaaaa tcagcatttta aataatagac tttccagcat  8275
tacagatgaa ataatttggc gcaggctttt taactgtcta ccatatttag aatgtggtgt   8335
caaaatgaga ttttttagaac tgctgtaaaa tattactaca ttactacaac gataacggcc 8395 taaaacaaca caaatttatt atcttacagc tctgtcagtc agacattcag caaagatctt   8455
agtcttggtg ggctacagaa tgtaggaggc atttcctgga tgcttccaag agagaatctt 8515 gctgttccct gcttctagag tcctttgctt agtttccttc catcttcaaa tccagcaacc  8575
tggtcaagac cttctcacat gacatcactg acttcctctt cttcctctcc cttacatatt  8635
taaggactca tgtgattaca atagctgcat ctgtgtaatc cagaataatc tcttcatctc  8695 aaggttttg ttctgttttg tttttttgtt ttgttttgtt ttgttttgtt ttgatggagt    8755
cttgctctgt cgtcaggctg gagtgcagtg gcgcgatctc ggctcactcc aacctccacc   8815
tcccgggttc aaaggattcc cctgcctcag cctctcgagt agctgggact acagatgcgt   8875
gctaccacac aaggctaata ttttgtattt tagtagagac gggatttcac catgttggcc   8935
aggatggtct ccgtctcctg acctcgtgat ctgcctgcct tggcctccca aagtgttggg  8995
attacaggca taagccattg cgccatgctc aaggttctta attacatctt taaaggccct   9055
ttttccatgt acagtaacat attcaatggt tctggggatt aggacttgga gccattattc   9115
tacctacaac aattagtatt ggacttccat catttctat cactcttgta atcgagaagg    9175
actatttcac tgggagtagc aagtcataat gtttgcgttg gcatttgtgt gggggttat    9235 cttcattcat taaataattg catgtaaaga aaattcctgt cactatttca aatgtttcat    9295
gtagttatta tagtgcttca gaatccaaag ggttatgtgt tacttatgta agatgagcag   9355
tctagggggt ggagaacagg tcatctagtg cagattcttc ctagctgaag tgtgttttct   9415
ctggggacaa ccaagtagga tttaattgtt ttgcttcctt ttttgggaac ttagacccat  9475
cttgcgatgt cctaagtctc caagcatctt atttgacctg cttatacaca tttgactaaa  9535
tagctaaata tgaccacatt gacgtggtaa agctttaaca cttttgtcca gattgaatca  9595
ctccatctgc tatcagttaa gcagtggaaa actgttatgg aaaagcaaac atgttttgat 9655 agatttaatg tgtaaagaag gtatccatac tctggaatgc tgctgatcaa taaatgagct 9715 gcaagacttt gttcgaaaca acactcaagc acaactgttt tactttccat accaagtttg  9775
```

-continued

```
gctgtgactg aatgaagaac atcagcattg atctttgctt tgcacttgta caagagacta    9835
tttgcagaga gccaaatata gcaacagagg atttaatatc ttgccaaaaa atacaaaatc    9895
tgttcccctt taagcatgac actctatcct ttcttgtgga tcttgctaaa aggaaaatat    9955
agctttaaac tccccctattc cttctgttga aagcttaaga atcttttca aatgagctat   10015 gtatggtttt gtggtatttt atgtttccaa aagaaaatgg ctacatgaaa aatctgtcca   10075
gtgttatcat ttttcttaca aaaaatactt ctagttatgg ttgtattaat taatttgatt   10135
gtgataatga ttacacaatg tttacctata tcaaatcatc atatcgtata ccttaaatat   10195
atataacttt tatgtgtcaa ttataactca gtaagtctgg gaaaatatcg ttaagtcaaa   10255
gattagagtc aacagaaata aagaaaaatc atactttgat aacttcagga ctaatcaagg   10315
atcaatgggt gacatgatat catgctatgt gccatttttgt gttaaacaaa ttacaccaac   10375
aataaaaaaa attggcttca a                                              10396
```

<210> SEQ ID NO 4
<211> LENGTH: 326
<212> TYPE: PRT
<213> ORGANISM: Homo sapiens

<400> SEQUENCE: 4

```
Met Ser Cys Ala Glu Val Met Tyr His Pro Gln Pro Tyr Gly Ala Ser
1               5                   10                  15

Gln Tyr Leu Pro Asn Pro Met Ala Ala Thr Thr Cys Pro Thr Ala Tyr
                20                  25                  30

Tyr Gln Pro Ala Pro Gln Pro Gly Gln Gln Lys Lys Leu Ala Val Phe
            35                  40                  45

Ser Lys Met Gln Asp Ser Leu Glu Val Thr Leu Pro Ser Lys Gln Glu
        50                  55                  60

Glu Glu Asp Glu Glu Glu Glu Glu Glu Lys Asp Gln Pro Ala Glu
65                  70                  75                  80

Met Glu Tyr Leu Asn Ser Arg Cys Val Leu Phe Thr Tyr Phe Gln Gly
                85                  90                  95

Asp Ile Gly Ser Val Val Asp Glu His Phe Ser Arg Ala Leu Gly Gln
            100                 105                 110

Ala Ile Thr Leu His Pro Glu Ser Ala Ile Ser Lys Ser Lys Met Gly
        115                 120                 125

Leu Thr Pro Leu Trp Arg Asp Ser Ser Ala Leu Ser Ser Gln Arg Asn
130                 135                 140

Ser Phe Pro Thr Ser Phe Trp Thr Ser Ser Tyr Gln Pro Pro Pro Ala
145                 150                 155                 160

Pro Cys Leu Gly Gly Val His Pro Asp Phe Gln Val Thr Gly Pro Pro
                165                 170                 175

Gly Thr Phe Ser Ala Ala Asp Pro Ser Pro Trp Pro Gly His Asn Leu
            180                 185                 190

His Gln Thr Gly Pro Ala Pro Pro Ala Val Ser Glu Ser Trp Pro
        195                 200                 205

Tyr Pro Leu Thr Ser Gln Val Ser Pro Ser Tyr Ser His Met His Asp
        210                 215                 220

Val Tyr Met Arg His His His Pro His Ala His Met His His Arg His
225                 230                 235                 240

Arg His His His His His His Pro Pro Ala Gly Ser Ala Leu Asp
                245                 250                 255
```

```
Pro Ser Tyr Gly Pro Leu Leu Met Pro Ser Val His Ala Ala Arg Ile
            260                 265                 270

Pro Ala Pro Gln Cys Asp Ile Thr Lys Thr Glu Pro Thr Val Thr
        275                 280                 285

Ser Ala Thr Ser Ala Trp Ala Gly Ala Phe His Gly Thr Val Asp Ile
        290                 295                 300

Val Pro Ser Val Gly Phe Asp Thr Gly Leu Gln His Gln Asp Lys Ser
305                 310                 315                 320

Lys Glu Ser Pro Trp Tyr
                325

<210> SEQ ID NO 5
<211> LENGTH: 24
<212> TYPE: DNA
<213> ORGANISM: Artificial
<220> FEATURE:
<223> OTHER INFORMATION: Primer VgII3-F

<400> SEQUENCE: 5
ggccacacaa aacagaaggt taag                                        24

<210> SEQ ID NO 6
<211> LENGTH: 25
<212> TYPE: DNA
<213> ORGANISM: Artificial
<220> FEATURE:
<223> OTHER INFORMATION: Primer VgII3-R

<400> SEQUENCE: 6
tcacccatga agttcacaat taaaa                                       25

<210> SEQ ID NO 7
<211> LENGTH: 20
<212> TYPE: DNA
<213> ORGANISM: Artificial
<220> FEATURE:
<223> OTHER INFORMATION: Primer hVgII3-F

<400> SEQUENCE: 7
tccccctgct gtgtctgagt                                             20

<210> SEQ ID NO 8
<211> LENGTH: 20
<212> TYPE: DNA
<213> ORGANISM: Artificial
<220> FEATURE:
<223> OTHER INFORMATION: Primer hVgII3-R

<400> SEQUENCE: 8
ggatgggctc acctgagatc                                             20

<210> SEQ ID NO 9
<211> LENGTH: 20
<212> TYPE: DNA
<213> ORGANISM: Artificial
<220> FEATURE:
<223> OTHER INFORMATION: Primer Cyclophilin A-F

<400> SEQUENCE: 9
ttttgacttg cgggcatttt                                             20

<210> SEQ ID NO 10
<211> LENGTH: 22
<212> TYPE: DNA
```

<213> ORGANISM: Artificial
<220> FEATURE:
<223> OTHER INFORMATION: Primer Cyclophilin A-R

<400> SEQUENCE: 10
ggacgctctc ctgagctaca ga                                              22

<210> SEQ ID NO 11
<211> LENGTH: 20
<212> TYPE: DNA
<213> ORGANISM: Artificial
<220> FEATURE:
<223> OTHER INFORMATION: Primer hCyclophilin A-F

<400> SEQUENCE: 11
ttcatctgca ctgccaagac                                                 20

<210> SEQ ID NO 12
<211> LENGTH: 20
<212> TYPE: DNA
<213> ORGANISM: Artificial
<220> FEATURE:
<223> OTHER INFORMATION: Primer hCyclophilin A-R

<400> SEQUENCE: 12
tcgagttgtc cacagtcagc                                                 20

<210> SEQ ID NO 13
<211> LENGTH: 19
<212> TYPE: DNA
<213> ORGANISM: Artificial
<220> FEATURE:
<223> OTHER INFORMATION: Primer Ap2-F

<400> SEQUENCE: 13
ccgcagacga caggaaggt                                                  19

<210> SEQ ID NO 14
<211> LENGTH: 15
<212> TYPE: DNA
<213> ORGANISM: Artificial
<220> FEATURE:
<223> OTHER INFORMATION: Primer Ap2-R

<400> SEQUENCE: 14
agggccccgc catct                                                      15

<210> SEQ ID NO 15
<211> LENGTH: 2491
<212> TYPE: DNA
<213> ORGANISM: Homo sapiens
<220> FEATURE:
<221> NAME/KEY: CDS
<222> LOCATION: (377)..(1339)

<400> SEQUENCE: 15
ggctgcccga cccgggcctg ggctgtggct gtgactggcg ctgccgtggg cgccgcagcc     60
ctcgcgggag ccggacgcgg taatgcccca gcggcgcagc gggcggctgc gtccctgagc    120
cgctatataa gcgcggcagg gaacatccgg aggggctgaa gatgaaggtg cccgcgcatg    180 ggccccccgct gattgccagt ccctcccgac cccgcgcccc gcgcggagcc cgaggccgcc    240
gaggacccgc cttcgccgca gtagcagctg gagcagcgac agaggcggca gctgcggcgg    300
cggcggcgcc cgcgccccctc gcgccagcgc gtagagcggc ggcggcagct cgggggccgc    360

```
cactgccccg gctgcc atg agt tgt gcg gag gtg atg tat cac ccc cag cct       412
               Met Ser Cys Ala Glu Val Met Tyr His Pro Gln Pro
                 1           5                  10 tat gga gcg tcc cag tat ctg ccc aac ccc atg gca gcg aca acc tgc         460
Tyr Gly Ala Ser Gln Tyr Leu Pro Asn Pro Met Ala Ala Thr Thr Cys
         15                  20                  25 ccc aca gcc tac tat cag ccg gcg ccc caa cct ggc cag cag aag aag         508
Pro Thr Ala Tyr Tyr Gln Pro Ala Pro Gln Pro Gly Gln Gln Lys Lys
     30                  35                  40 tta gcg gta ttc agc aag atg cag gac tct ctg gaa gtc acc ctt ccc         556
Leu Ala Val Phe Ser Lys Met Gln Asp Ser Leu Glu Val Thr Leu Pro
45                  50                  55                  60 agc aaa caa gag gag gag gat gag gag gag gag gag gag aaa gac             604
Ser Lys Gln Glu Glu Glu Asp Glu Glu Glu Glu Glu Glu Lys Asp
                 65                  70                  75 cag cct gcc gag atg gag tac ctt aac tct cgc tgt gtc ctt ttc act         652
Gln Pro Ala Glu Met Glu Tyr Leu Asn Ser Arg Cys Val Leu Phe Thr
                     80                  85                  90 tat ttc cag gga gac att ggg tca gta gtg gat gaa cac ttc tca aga         700
Tyr Phe Gln Gly Asp Ile Gly Ser Val Val Asp Glu His Phe Ser Arg
             95                 100                 105 gct ttg ggc caa gcc atc acc ctc cat cca gaa tct gcc att tca aaa         748
Ala Leu Gly Gln Ala Ile Thr Leu His Pro Glu Ser Ala Ile Ser Lys
     110                 115                 120 agc aag atg ggg cta acc ccc cta tgg cga gac agc tca gct ctc tca         796
Ser Lys Met Gly Leu Thr Pro Leu Trp Arg Asp Ser Ser Ala Leu Ser
125                 130                 135                 140 agc cag cgg aat agt ttc cca act tcc ttt tgg acc agc tct tac cag         844
Ser Gln Arg Asn Ser Phe Pro Thr Ser Phe Trp Thr Ser Ser Tyr Gln
                 145                 150                 155 ccc cca cct gca cct tgt ttg ggg gga gtt cat cct gac ttc cag gtc         892
Pro Pro Pro Ala Pro Cys Leu Gly Gly Val His Pro Asp Phe Gln Val
                     160                 165                 170 act gga ccc cct ggc acc ttt tct gca gct gat ccc agt cct tgg ccg         940
Thr Gly Pro Pro Gly Thr Phe Ser Ala Ala Asp Pro Ser Pro Trp Pro
             175                 180                 185 gga cac aac ctg cat cag act ggc cca gcc cct ccc cct gct gtg tct         988
Gly His Asn Leu His Gln Thr Gly Pro Ala Pro Pro Pro Ala Val Ser
     190                 195                 200 gag tcc tgg cct tat cct ttg aca tct cag gtg agc cca tcc tac agc        1036
Glu Ser Trp Pro Tyr Pro Leu Thr Ser Gln Val Ser Pro Ser Tyr Ser
205                 210                 215                 220 cat atg cat gac gtg tac atg cgg cac cac cac cct cat gcc cac atg        1084
His Met His Asp Val Tyr Met Arg His His His Pro His Ala His Met
                 225                 230                 235 cac cac cgc cac cgc cac cat cat cac cat cac cac cct cct gct ggc        1132
His His Arg His Arg His His His His His His His Pro Pro Ala Gly
                     240                 245                 250 tct gcc ctg gat cca tcc tat ggg cct ctg ctg atg cct tca gtg cat        1180
Ser Ala Leu Asp Pro Ser Tyr Gly Pro Leu Leu Met Pro Ser Val His
             255                 260                 265 gcg gcc agg att cct gct ccc cag tgt gac atc aca aag aca gaa cca        1228
Ala Ala Arg Ile Pro Ala Pro Gln Cys Asp Ile Thr Lys Thr Glu Pro
     270                 275                 280 act aca gtc acc tct gct acc tca gca tgg gct gga gcc ttt cat gga        1276
Thr Thr Val Thr Ser Ala Thr Ser Ala Trp Ala Gly Ala Phe His Gly
285                 290                 295                 300 aca gta gac ata gtg ccc agc gtg gga ttc gat aca ggc tgg agt gca        1324
Thr Val Asp Ile Val Pro Ser Val Gly Phe Asp Thr Gly Trp Ser Ala
                 305                 310                 315
```

```
atg gcg aga tct tga ctcactgcaa cctctgcctc ccgagttcaa ccaattgtcc    1379
Met Ala Arg Ser
        320 tgcctcagcc acctgagtag ctggaattac aggcatctgc caccacgccc ggctaatttt    1439
ttgtattttt agtagatagt cactattttg aatagtgaag gctggcttcc ctattttgaa    1499
tagtgaaggc tggcttccct attttgaata gtgaaggctg gcttccctat tttggccagg    1559
ctggtctcaa actcctgacc tcgtgatcca cctgcctcgg actcccaagg tgctgggatt    1619
acaggtgtga gccactgtgt ccagccctca tgtacaaatt tttaagtaaa tgtgtgttta    1679
attctcttgg aaatatatct aggagtagaa ctgtggggtt aagagaacct cactttttat    1739
tttatgtatt tctatatttt ttgaattttt tcaaagagc atatatatgc aattttaaa    1799
atatttaaat ttaaatttt gttttttaaa tttttttta gtatttaaat tgttaagatt    1859
cattacaaca tattatagta gagtttgagg tttggtaggc aaaactgcca taggaatgaa    1919
gtaaggtggt ccattttttc cgaagggctg agtggtggtg aggacagtga ggtgcctctg    1979
gcacaaaatt taaaaggatc catactgtga gggctgtgca agtgtatgcc accccatatt    2039
ttgcacccag ggctcctat tcctctaacc tctgtcttgg tgttgctttg ctgtcatgcg    2099
agctcactct tactttttgc tccctctgtt gaacaggtat tacatacagg taccttgaaa    2159
tgatcagtat ggtatgatca taagtcattt gtatttgccc tccacgtgaa aaatgctcat    2219
ctttaccaag aggctgttat cacaaatctc acattaggct ttttcccttt cctttatcag    2279
tctttaaact gagtttcatg ggttccatag gaaaaatact cagaatgtga taataagggc    2339
ttaattgaaa aagaaaaga tctattatca aatgaattta tttacattgc ctaccatata    2399
cctcttagag atcacagttc cctatagcat ataaaatgtt ttatatattc ttcagtaaaa    2459
aagcatttta aattgtaaaa aaaaaaaaaa aa                                  2491
```

<210> SEQ ID NO 16
<211> LENGTH: 320
<212> TYPE: PRT
<213> ORGANISM: Homo sapiens

<400> SEQUENCE: 16

```
Met Ser Cys Ala Glu Val Met Tyr His Pro Gln Pro Tyr Gly Ala Ser
1               5                   10                  15

Gln Tyr Leu Pro Asn Pro Met Ala Ala Thr Thr Cys Pro Thr Ala Tyr
            20                  25                  30

Tyr Gln Pro Ala Pro Gln Pro Gly Gln Gln Lys Lys Leu Ala Val Phe
        35                  40                  45

Ser Lys Met Gln Asp Ser Leu Glu Val Thr Leu Pro Ser Lys Gln Glu
    50                  55                  60

Glu Glu Asp Glu Glu Glu Glu Glu Lys Asp Gln Pro Ala Glu
65                  70                  75                  80

Met Glu Tyr Leu Asn Ser Arg Cys Val Leu Phe Thr Tyr Phe Gln Gly
                85                  90                  95

Asp Ile Gly Ser Val Val Asp Glu His Phe Ser Arg Ala Leu Gly Gln
            100                 105                 110

Ala Ile Thr Leu His Pro Glu Ser Ala Ile Ser Lys Ser Lys Met Gly
        115                 120                 125

Leu Thr Pro Leu Trp Arg Asp Ser Ser Ala Leu Ser Ser Gln Arg Asn
    130                 135                 140

Ser Phe Pro Thr Ser Phe Trp Thr Ser Ser Tyr Gln Pro Pro Pro Ala
```

|     |     |     |     |     |     |     |     |     |     |     |     |     |     |     |     |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |
| Pro | Cys | Leu | Gly | Gly | Val | His | Pro | Asp | Phe | Gln | Val | Thr | Gly | Pro | Pro |
|     |     |     |     | 165 |     |     |     |     | 170 |     |     |     |     | 175 |     |
| Gly | Thr | Phe | Ser | Ala | Ala | Asp | Pro | Ser | Pro | Trp | Pro | Gly | His | Asn | Leu |
|     |     |     | 180 |     |     |     |     | 185 |     |     |     |     | 190 |     |     |
| His | Gln | Thr | Gly | Pro | Ala | Pro | Pro | Ala | Val | Ser | Glu | Ser | Trp | Pro |     |
|     |     | 195 |     |     |     |     | 200 |     |     |     |     | 205 |     |     |     |
| Tyr | Pro | Leu | Thr | Ser | Gln | Val | Ser | Pro | Ser | Tyr | Ser | His | Met | His | Asp |
|     | 210 |     |     |     |     | 215 |     |     |     |     | 220 |     |     |     |     |
| Val | Tyr | Met | Arg | His | His | His | Pro | His | Ala | His | Met | His | His | Arg | His |
| 225 |     |     |     |     | 230 |     |     |     |     | 235 |     |     |     |     | 240 |
| Arg | His | His | His | His | His | His | Pro | Pro | Ala | Gly | Ser | Ala | Leu | Asp |     |
|     |     |     |     | 245 |     |     |     |     | 250 |     |     |     |     | 255 |     |
| Pro | Ser | Tyr | Gly | Pro | Leu | Leu | Met | Pro | Ser | Val | His | Ala | Ala | Arg | Ile |
|     |     |     | 260 |     |     |     |     | 265 |     |     |     |     | 270 |     |     |
| Pro | Ala | Pro | Gln | Cys | Asp | Ile | Thr | Lys | Thr | Glu | Pro | Thr | Thr | Val | Thr |
|     |     | 275 |     |     |     |     | 280 |     |     |     |     | 285 |     |     |     |
| Ser | Ala | Thr | Ser | Ala | Trp | Ala | Gly | Ala | Phe | His | Gly | Thr | Val | Asp | Ile |
|     | 290 |     |     |     |     | 295 |     |     |     |     | 300 |     |     |     |     |
| Val | Pro | Ser | Val | Gly | Phe | Asp | Thr | Gly | Trp | Ser | Ala | Met | Ala | Arg | Ser |
| 305 |     |     |     |     | 310 |     |     |     |     | 315 |     |     |     |     | 320 |

```
<210> SEQ ID NO 17
<211> LENGTH: 2000
<212> TYPE: DNA
<213> ORGANISM: Homo sapiens
<220> FEATURE:
<221> NAME/KEY: promoter
<222> LOCATION: (1)..(2000)

<400> SEQUENCE: 17
atctgcatta gtgtgctagg gctgtcataa ataccacaaa ctaggtggcc taaaaaaaca    60
aattaagctg ggcataccgt ggctcacgcc tgtaatccca gtactttggg aggccgaggt   120
gggcggatca cctgaagtca ggagttcaag atcatcctgg ccaacatggt gaaaccctgt   180
ctctacaaaa gtacaaaaat tagccgggca tgatggcggg tgcctgtaat cccagctact   240
cgggaggctg ggcggaaga atcacttgaa ccgggaggag gttgcagtga gccgagatcg   300
tgacattgca ctccagcctg gcaacagag cgatactccg tctcaaaaaa aaaaaaaaa    360
aaaaaagtt aatttttca tagttctgga ggatagaagc acaagataag gtgtggtcag    420
tgttggtttc aaggtgagac ctttcttctt ggcttgtagg taactcacta tgacttcaga   480
tggtctttcc tctttgacag agcagagaga cagggagtgg ggtttggggg agacatagat   540
atctctggcg tgttttctct tcttataagg aacctagtcc tattagatta gggcccaacc   600
ttttaaatct catttaacct tatcacctcc ttatatgtcc tgtcttcaaa tacagccata   660
ttgtgggtta gggcttcaat atatacattt ttgggaagac ataattcaaa ctataaaaac   720
attagtgcat ttgactttca aactgactt ttctctgaga aaagatagac tgtaaaaatg    780
agagattgct gtgagtcata aaagaggatg cctacgtata aggagagata tgtttgctga   840
atctcagagc tagagtttgc tcatttataa aatgaggccc agtgcggtgc ctcatgcctg   900
ttatcccagc actttgggag accgaggcag aaggatcact tgaggccagg agttggagac   960
cagcctagga acatagcaa gacccttcct ctataaaaaa aaaattaaa aaaattacct   1020
gggcgtggta atgcacgcct gtagtcccag ctactccaga ggctgagatg ggaggatctc  1080
```

```
ttgagcgtgg gggtggtagc tgcagtgagc tgtgctcatg tcactgtact ctagcttggg   1140
cggcagaagg aaaccctatc tcaaaataaa taaaataatg tgagtataat tatttctact   1200
gattatgtca gaatacaagt atattctcac agacgttttt ttccccattt tggagagggt   1260
cagatccaat tgcaaagaga taaacccttta ttagcgaatg ggcttaatca actacccttt   1320
attgctctgt gaaaaccagg ctgtaaaagc cagaaatggt ggacgtctca cagcagtgtc   1380
ataccatgaa gatgtaaact taaagcgagg attgcttgtg gaaaactgtg ttgcattctt   1440
ggcatgtggg cacttgcaga gatgttaact ttcacttatg attattttaa tgtaggagct   1500 aatcccgtg tattctgcgc ctgctctgtt ttacccettt gtacactcgg cttttgtttg    1560
gtcccagcct ctgagttggt gttccctgta aaatctcctt ggagtaggga agccctcgcc   1620
ctggcggcca ggtgacagag acagggtggg aacctgccga gccttgaggg gcggagcct   1680 ctgcatacca ttcccctccc accaccatcc catgctggga ggcggagagg gctgcaaact   1740
tcgctccaat ccgcagccag ccttccccgg ggtcccctg cagggtgacc cgcccgctgc    1800
aaagcgagtt ggagaaaactt tgcaaagttc cgcgtcagag cctggggagg caaagtgctc   1860
ccccttctcc ccggcgttcc ccctccctct gccccgcct cctgtcctc gcacagccgg     1920 gagcaccgt gataggacga gccccgggcg tgcattgtgt atatgcaaac cggagctggg    1980
ctccccacgg ctgcccgacc                                                2000

<210> SEQ ID NO 18
<211> LENGTH: 1957
<212> TYPE: DNA
<213> ORGANISM: Mus sp.
<220> FEATURE:
<221> NAME/KEY: promoter
<222> LOCATION: (1)..(1957)

<400> SEQUENCE: 18
cattctctct ctctctctct ctctctctct ctctctctct ctctgtctcc                60
cctccctccc tctctccctc cctctctccc tccctccttc tctccatctc cccttctgt    120 ctcaaaaaaa gaaacaacaa caacaaaata caacaaacaa gacacaagta agataaaaaa    180
aattccagaa caaaacaaaa agcccaccag aagcacagtg tctgtgttgt tagccaagta    240
cttcttcctg gtcatgtggc ttgccctgta atgtggttga gagaccgagt gactacactg    300
gagaaagtgg atttctcctt tgccaacaga taacaaaaat actttaaagg tctatcctgt    360
cagttttaat tcataactga tctgaagtaa agaaaaataa taaacctggt ttaaaaaaat    420
gatacgaaac ctactccaat tctattcttt aaccttgtat tggcaaattt cagtctttaa    480
acttatgtat aaaataagaa cccatgttac ttatgtgttt ttattatatg ttttaatatc    540
aggtttcata actcatctga gttcttcagt cccaagacta gtcaggttga acagtccatt    600
ttatgtgaca aatttgttta aatatcacca tgaaacacac cagttacttg gactgaagca    660
gggtccttta aaaatgtcag gaagaaaagt gactttatg ttttatcgtt atttgaaaat     720
ggtacaaagt tcgccaaact ttcttcacat aaaagcagtt taaaaaatta gaacattggc    780
aacagcctat ggagtgaaaa gaaaatgggt ttcagtgaaa ataaagtgcc ccagtgttct    840
agggtggccc agaagctccc gaagcgagag tggctcacag tatatcatcc tcacagagct    900
aacacacttc ttggttgata atcatttata attgcatcgc agttcttttc agttgttaca    960
gggtttcctc tccacacaac ctttggataa ttgcttccaa ttttctacaa ttagtatttt   1020
ttttaaaaca ttttaaaagg aatctacatc aaatatttacc ataggctttc tatttttttg   1080
```

-continued

```
ggggggggt tgttggtttt tcgagacaga gtttctctgt gtagccctgg ctgtcctgga    1140
actcactttg tagaccaggc tggcctcgaa ctcagaaatc cacctgcctc tgcctcccga    1200
gtgctgggat taaaggcgag cgccaccatg cccggctacc ataggctttc ttacagaagg    1260
tattctaaat tagacaagct catatttttt aatcaacctt gaaggacaac ttttttgaaa    1320
tatgacagaa agtgcagact ccacaaagac ggttcaaaca cttccagtat agattaagag    1380
cctgcagaaa tcccatactc taccactgca tcattataga taaataaatc tcttgtgcac    1440
ccggatctta taaagtctat caaaatagaa ctgctgatta ttttaaactt gaaagtcatg    1500
tcccaattat tattttacac ttctgttttt aatatcttca tcaagctctc tcttactttt    1560
ccccattaac cttttgtttt tctcctccct ggtgcttgtc caggttgctg cttcatttaa    1620
agttctcagc ccgttgttga ctcctgaacc atctgtgaca gacaccatcg cactgtcagc    1680
cagctgcact gaagtgtgac agcattgctt tccttcctgc aattaggttt ttctctctta    1740
aagagttaag ggcatttgct gtttatctat gctggggtga ttgtaaggac caggtcgatt    1800
tagctgtcag tgaactaaaa catttataaa tagcacagga taaaagaatg ttacagtttt    1860
attttatttc ggtcaccta aagacaaata tcaattgcag tcacctgcag tcacatctgc    1920
tttgctcctg aggatgaggg ctagtaactg cagggct                            1957
```